(12) United States Patent
Gosselin et al.

(10) Patent No.: US 6,743,595 B1
(45) Date of Patent: Jun. 1, 2004

(54) METHOD AND DIAGNOSTIC KIT FOR DIAGNOSIS OF ENDOMETRIOSIS

(75) Inventors: Diane Gosselin, Pointe Calumet (CA); Danièle Gagné, Montréal (CA); Patrice Hugo, Sainte Dorothée/Laval (CA); Pierre Miron, Laval (CA)

(73) Assignee: Metriogene Biosciences Inc., Quebec (CA)

( * ) Notice: Subject to any disclaimer, the term of this patent is extended or adjusted under 35 U.S.C. 154(b) by 0 days.

(21) Appl. No.: 09/489,909

(22) Filed: Jan. 24, 2000

Related U.S. Application Data (60) Provisional application No. 60/117,031, filed on Jan. 25, 1999.

(51) Int. Cl.[7] ............................................. G01N 33/53
(52) U.S. Cl. ................. 435/7.24; 435/7.1; 435/7.2; 435/7.21; 435/7.23; 435/7.4; 435/7.5; 435/7.92; 435/7.94; 435/287.2; 435/960; 435/975; 436/503; 436/519; 436/547; 436/548; 436/63; 436/64; 436/172
(58) Field of Search ............................. 435/7.2, 7.21, 435/7.23, 7.1, 7.24, 6, 7.92, 7.4, 7.94, 7.5, 287.2, 960, 975; 436/503, 519, 547, 548, 63, 64, 172

(56) References Cited

U.S. PATENT DOCUMENTS

| | | | |
|---|---|---|---|
| 5,478,725 A | 12/1995 | Lessey | 435/7.21 |
| 5,618,680 A | * 4/1997 | Miron et al. | 435/7.21 |
| 5,831,035 A | * 11/1998 | Timms | 530/389.1 |
| 6,309,843 B1 | * 10/2001 | Timms | 435/7.21 |

FOREIGN PATENT DOCUMENTS

| | | | |
|---|---|---|---|
| EP | 0 387 027 | 9/1990 | |
| WO | WO 92/18535 | 10/1992 | ........... C07K/15/00 |
| WO | WO 94/28021 | 12/1994 | ........... C07K/15/00 |
| WO | WO 96/20404 | 7/1996 | |
| WO | WO 98/10291 | 3/1998 | |

OTHER PUBLICATIONS

Bulmer et al., Intraepithelial leucocytes in endometriosis and adenomyosis: Comparison of eutopic and ectopic endometrium with normal endometrium, Human Reproduction 13(10): 2910–2915 (1998).*

Witz et al., Characterization of lymphocyte subpopulations and T–cell activation in endometriosis, American Journal of Reproductive Immunology 32 (3): 173–179 (Oct. 1994).*

Pang et al., Morphological and phenotypic and functional characteristics of a pure population of CD56+ CD16– CD3– large granular lymphocytes generated from human duodenal mucosa, Immunology, 79 (3): 498–505 (Jul., 1993).*

Jones R K; Phenotypic and functional studies of leukocytes in human endometrium and endometriosis. Human Reproduction Update, (Sep.–Oct. 1998) 4 (5) 702–9.*

Jones R K; Immunohistochemical characterization of stromal leukocytes in ovarian endometriosis: comparison of eutopic and ectopic endometrium with normal endometrium. Fertility and Sterility, (Jul. 1996) 66 (1) 81–9.*

(List continued on next page.)

*Primary Examiner*—Christopher L. Chin
*Assistant Examiner*—Gailene R. Gabel
(74) *Attorney, Agent, or Firm*—Crowell & Moring LLP

(57) ABSTRACT

The invention relates to a method and a kit for the diagnosis of endometriosis using blood and endometrial leukocyte markers or a combination thereof. The marker is a surface antigen from endometrial or blood leukocytes.

3 Claims, 1 Drawing Sheet

OTHER PUBLICATIONS

Oosterlynck D.J. et al., *Am. J. Reprod. Immunol.* 31: 25–31, 1994.
Becker J.L. et al., *Am. J. Reprod. Immunol.,* 34: 179–187, 1995.
Wu M.Y. et al., *Am. J. Reprod. Immunol.* 35: 510–516, 1996.
Ho H.N. et al., *Hum. Reprod.,* 97: 2528–2533, 1997.
Ota H. et al., *Am. J. Reprod. Immunol.,* 35: 477–482, 1996.
Klentzeris L.D. et al., *Eur. J. Obstet. Gynecol. Reprod. Biol.,* 63: 41–47, 1995.
Jones R.K. et al., *Fertil. Steril.,* 66: 81–89, 1996.
Cruse et al., "Illustrated Dictionary of Immunology", (XP–002136669) 1995, pp. 53–62.

Oosterlynck et al., "Flow Cytometry Analysis of Lymphocyte Subpopulations in Peritoneal Fluid of Women With Endometriosis", American Journal of Reproductive Immunology, vol. 31, No. 1, Jan. 1, 1994 (XP 000568653), pp. 25–31.

Oosterlynck et al., "Immunohistochemical Characterization of Leucocyte Subpopulations in Endometriotic Lesions", Archives of Gynecology and Obstetrics, 1993 (XP 000568666), pp. 197–206.

* cited by examiner

Fig. 1

METHOD AND DIAGNOSTIC KIT FOR DIAGNOSIS OF ENDOMETRIOSIS

This application claims the benefit of provisional application No. 60/117,031 filed Jan. 25, 1999.

BACKGROUND OF THE INVENTION (a) Field of the Invention

The invention relates to a method and a kit for the diagnosis of endometriosis using blood and endometrial leukocyte markers.

(b) Description of Prior Art

Endometriosis is one of the most common gynecological disorders, affecting up to 15% of women within reproductive age. It is closely associated with severe pelvic pain, dysmenorrhea, dyspareunia, infertility and several other symptoms such as intraperitoneal bleeding, back pain, constipation and/or diarrhea. It is a major threat to physical, psychological and social integrity of the patients.

Endometriosis is characterized by the implantation and growth of endometrial cells (which normally constitute the lining of the uterus) in extra-uterine sites such as the peritoneal cavity. Although the etiology and pathogenesis of endometriosis remain mainly unclear, the theory of retrograde menstruation is the most widely accepted to explain the presence of ectopic endometrial cells in the peritoneal cavity. However, this phenomenon occurs in most women and, thus, several other factors must be invoked to explain the implantation of endometrial cells and the subsequent development of endometriotic lesions. It is generally believed that initiation of endometriosis implies a complex cascade of events requiring several essential features. Retrogradely seeded endometrial cells must remain viable, be capable of adhering to the mesothelium and of proliferating. Local degradation of the extracellular matrix, as well as extensive vascularization, are also believed to play an essential role in promoting the invasion of the peritoneal cavity by endometrial cells. Furthermore, once implanted, ectopic endometrial cells must have the capacity to counteract the cytolytic action of the immune system. Indeed, this is supported by the observation of several immunological abnormalities in patients with endometriosis.

At present, direct visualization of the endometriotic lesions under surgical procedures (laparascopy or laparotomy) is the golden standard and the only reliable method available to diagnose endometriosis. However, this method is highly invasive (i.e. surgery under general anesthesia), costly (i.e. direct cost and indirect cost due to convalescence) and requires a well-trained surgeon who has the ability to identify endometriotic lesions with a variety of appearances. The type of lesions, their size and their localization will determine the stage of the disease (stage I minimal, stage II mild, stage III moderate, stage IV severe). However, there is still no clear consensus on how these parameters correlate with the stage of the disease and the prognostic of endometriosis. In addition, early or minimal endometriosis (which can involve microlesions) can be hardly diagnosed by surgical methods, as they are unlikely to be detected by direct visualization. Indeed, several studies have reported microscopic endometriotic lesions that were not detected laparoscopically. Because the diagnosis of endometriosis by surgical procedures is difficult, costly and invasive, in some cases, several physicians and patients tend to avoid it or at least seriously delay it. Hence, the length of time between the onset of symptoms and the diagnosis can be as long as 8 to 12 years. The possibility to diagnose endometriosis at an early stage would certainly improve the efficacy of the treatments, and reduce dramatically the number of years during which patients endure acute or chronic pain.

Imaging methods such as transvaginal ultrasound and magnetic resonance imaging have been designed for the diagnosis of endometriosis. However, these techniques can only be reliable for the detection of large (>1 cm diameter) endometriomas lesions detected among a very small proportion of patients with endometriosis. Moreover, the high cost of these techniques has limited their use for the diagnosis of endometriosis.

Serum proteins such as CA-125 and placental protein-14 have been proposed as diagnostic markers for endometriosis. Elevated levels of CA-125 have been observed in serum, menstrual effluent and peritoneal fluid of patients with endometriosis. However, these markers, when used alone, are of very limited value for a diagnosis test. Indeed, these markers are not suitable for screening or diagnostic purposes because they provide poor sensitivity. Furthermore, levels of CA-125 and placental protein-14 vary according to several factors such as the assay, the stage of the disease and the menstrual cycle. Finally these markers are known to be modulated by conditions other than endometriosis.

High concentrations of antibodies to endometrial antigens were found in the serum of patients with endometriosis, and thus were proposed as markers for a diagnostic test (International patent application publications WO 94/28021 and WO 92/18535). However, the levels of specificity and sensibility with these tests remain very low. In most cases, the antigens recognized by these antibodies are still poorly characterized or yet totally unknown.

In U.S. Pat. No. 5,478,725, low levels of $\alpha v \beta 3$ integrin expression in endometrial samples during the secretory phase of the menstrual cycle is described as a predictor of endometriosis in infertile but not in fertile patients with endometriosis. This observation was associated with milder form of endometriosis (stages I and II) only and, thus, is not useful to detect advanced stages of the disease. Moreover, this method yielded a specificity of 91% but a very low sensitivity (38%).

Taking into account that a number immunological abnormalities have been reported in patients with endometriosis, it is conceivable that the proportion of leukocyte populations and/or their activation status may be modulated during the course of the disease and, thus, may provide some diagnostic value. Previous flow cytometric studies have shown that some T lymphocyte subpopulations (CD8+, CD45+/HLADR+, CD45+/CD3+/HLADR+or CD3+/CD25+) can be slightly modulated in the peritoneal fluid of subjects with endometriosis relative to normal controls (Oosterlyncck D. J., et al., Am J reprod. Immunol., 31: 25–31, 1994; Becker J. L., et al., Am J Reprod. Immunol., 34: 179–187, 1995; Wu M. Y., et al., Am. j. Reprod. Immunol. 35: 510–516, 1996). However, these observations have limited value for the diagnosis of endometriosis because peritoneal fluid collection is an invasive, non-conventional procedure. Proportions of leukocyte populations have also been studied in peripheral blood and endometrium of patients with endometriosis. Wu et al., (supra) have reported a modest but significant decrease in the proportion of CD3+ T lymphocytes expressing either CD69 or CD25 activation marker in the blood of patients with advanced endometriosis but not in patients with mild stage of endometriosis or normal controls. This difference was observed in advanced cases of endometriosis only and it was too modest to be used as a diagnostic marker. In contrast, Oosterlynck et al., (Oosterlynck D. J., et al., *Am J reprod. Immunol.*, 31: 25–31, 1994) and Ho et al. (Ho H. N., et al., *Hum Reprod.*, 97: 2528–2533, 1997) reported no significant difference in term of T lymphocyte subpopulations when comparing endometriosis subjects with normal controls. These inconsistent results may be explained by the very low number of samples tested in these studies.

Several studies have investigated whether leukocytes are also modulated in eutopic endometrium from patients with endometriosis. Results arising from these studies are contradictory, probably due to the fact that in most cases the methods used were only semi-quantitative and the number of samples tested were very low. For instance, by means of immunohistochemistry, Ota et al. (Ota H., et al., *Am J Reprod. Immunol.*, 35: 477–482, 1996) have reported that the number of CD3+, CD4+, or CD8+ T lymphocytes, cells bearing adhesion molecules (i.e. ICAM-1, LFA-1, CD2) or CD68+ cells were upregulated in the endometrium of patients with endometriosis compared with infertile controls. In contrast, several other studies using similar techniques have reported no difference in the proportion of T lymphocyte subsets (Klentzeris L. D., et al., *Eur. J Obstet gynecol Reprod Biol.*, 63:41–47, 1995; Jones R. K., et al., *Fertil Steril*, 66:81–89, 1996). In addition, a decrease in CD3 positive T cells has been shown by flow cytometry analysis but no difference in the proportion of CD4+, CD8+ stromal leukocytes in the endometrium of patients with endometriosis compared with fertile controls. When these observations are tentatively used in a diagnostic test, they give only low levels of sensibility and specificity because of a significant overlap between the groups.

Therefore, the diagnostic methods presented in the literature so far do not solve the problems encountered with the diagnosis of endometriosis by surgical procedures. It thus remains imperative to be provided with a less invasive, cheaper and reliable method that could allow detection of females suffering from endometriosis as early as possible.

SUMMARY OF THE INVENTION

One aim of the present invention is to provide a less invasive, cheaper and reliable method that could allow detection of females suffering from endometriosis as early as possible.

In accordance with the present invention there is provided a specific blood and/or endometrial leukocyte marker for endometriosis selected from the group consisting of CD3+, CD4+, CD5+, CD8+, CD13+, CD14+, CD20+, CD36+, CD44+, CD56+, CD57+, CD69+, CD122+, HLADR+, CD16+, CD45RA+, CD45RO+, CD56−CD122+, CD3+ CD4−CD69+, CD3−CD8+HLADR−, CD3+CD4+, CD3+ CD4−, CD3−CD4−, CD3+CD5+, CD3−CD5+, CD3−CD5−, CD3+CD8+, CD3+CD8−, CD3−CD8−, CD3+CD16+, CD3−CD16+, CD3+CD16−, CD3−CD20+, CD3−CD20−, CD3+CD44−, CD3−CD44+, CD3−CD44−, CD3+ CD45RA−, CD3−CD45RA−, CD3+CD45RA+, CD3+ CD45RO+, CD3−CD45RO+, CD3+CD45RO−, CD3+ CD56−, CD3−CD56−, CD3+CD57−, CD3−CD57+, CD3− CD57−, CD3+CD69−, CD3+CD69+, CD3−CD69+, CD3+ CD122−, CD3+HLADR+, CD3+HLADR−, CD3− HLADR+, CD3−HLADR−, CD4+CD13+, CD4+CD13−, CD4−CD13+, CD4+CD14−, CD4−CD14−, CD4−CD16−, CD4−CD36+, CD4+CD45RA−, CD4−CD45RA−, CD4+ CD45RO+, CD4+CD45RO−, CD4−CD45RO+, CD4+ CD69−, CD4−CD69+, CD4−CD69−, CD4+HLADR−, CD4-HLADR+, CD8−CD44+, CD8−CD44−, CD8+CD69−, CD8+HLADR−, CD8−HLADR−, CD13+CD16−, CD13− CD16+, CD13+CD44+, CD13−CD44−, CD13+CD45RO−, CD13−CD45RO+, CD13−CD69+, CD13−CD122+, CD13− CD122−, CD13+HLADR+, CD13−HLADR+, CD14+ CD13+, CD14+CD13−, CD14+CD16−, CD14+CD44+, CD14−CD44−, CD14+CD45RO+, CD14−CD69−, CD14+ CD122−, CD14+HLADR+, CD14−HLADR+, CD20− CD5+, CD20−CD5−, CD20+CD44−, CD20−CD44+, CD20−CD44−, CD20−CD69+, CD20−CD69−, CD20+ HLADR+, CD20−HLADR+, CD20−HlADR−, CD36− HLADR+, CD56−CD16+, CD56−CD16−, CD56−CD44−, CD56+CD69−, CD56−CD69+, CD56−CD69−, CD56+ CD122+, CD56+CD122−, CD56−CD122−, CD56+ HLADR+, CD57−CD44+, CD57−CD44−, CD3−CD4− CD44+, CD3−CD4+CD45RA−, CD3−CD4−CD45RA+, CD3−CD4−CD45RA−, CD3−CD4−CD45RO+, CD3− CD8−CD44+, CD3+CD8+CD69−, CD3+CD8+HLADR−, CD3+CD8−HLADR+, CD3+CD8−HLADR−, CD3−CD8− HLADR−, CD3+CD20−CD5+, CD3+CD20−CD5−, CD3− CD20−CD5−, CD3+CD56+CD16+, CD3+CD56−CD16+, CD3+CD56−CD16−, CD3−CD56+CD16+, CD3−CD56+ CD16−, CD3+CD56−CD44+, CD3+CD56−CD44−, CD3+ CD56−CD122+, CD3+CD56−CD122−, CD3−CD56+ CD122+, CD3−CD56−CD122−, CD3−CD56−HLADR−, CD3−CD57+CD44−, CD3−CD57−CD44+, CD3−CD57− CD44−, CD3+CD57−HLADR+, CD4−CD13+CD16+, CD4−CD13−CD16+, CD4−CD13−CD16−, CD14+CD13+ CD16b+, CD14+CD13+CD16b−, CD14+CD13−CD16b−, CD14−CD13−HLADR+, CD14−CD13−HLADR−, CD14+ CD20+CD44+, CD14+CD20+CD44−, CD14+CD20− CD44+, CD14+CD20−CD44−, CD14−CD20+CD44−, ratio CD3/CD45RO, Ratio CD13/CD3, Ratio CD13/CD8, Ratio CD14/CD3, and Ratio CD14/CD8.

Also in accordance with the present invention, there is provided a diagnostic method for the detection of endometriosis in a patient sample. The method comprises the step of detecting at least one specific marker as described above, whereby detection of this specific marker is indicative of endometriosis.

Further in accordance with the present invention, there is provided a diagnostic method for the detection of endometriosis in a patient sample. The method comprises the step of detecting at least two different surface antigens from blood or endometrial leukocytes, whereby detection of at least two different surface antigens is indicative of endometriosis.

In accordance with a further embodiment of the invention, there is provided a diagnostic method for the detection of endometriosis in a patient sample. The method comprises the step of detecting a specific marker combination for endometriosis as defined above, whereby detection of this combination is indicative of endometriosis.

Further in accordance with the present invention, there is provided a diagnostic kit for the detection of endometriosis. The kit comprises an antibody specific for the specific maker as described above. Preferably, the kit comprises at least two different antibodies, each specific for different surface antigens as defined in the specific marker combination defined above. Most preferably, the specific marker combination of the diagnostic kit is selected from the combination described below in Tables 1 and 2.

For the purpose of the present invention, the following symbol "/" is intended to mean a ratio between an expression in front of the symbol and another expression after the symbol.

DETAILED DESCRIPTION OF THE INVENTION

In accordance with the present invention, there is provided reliable diagnostic test for endometriosis that is less invasive and less costly than the actual surgical procedure accepted as the golden standard. An extensive study was undertaken by means of flow cytometric analysis, in which the proportion of several blood and endometrial leukocyte subsets was compared in patients with endometriosis and normal controls.

The present invention identifies a series of leukocyte subsets that can be used as markers in a diagnostic test for endometriosis. These leukocyte subsets are defined according to the expression of cell surface antigens. Several cell surface antigens may define the same population of cells, and thus they are included in the present invention.

Any other antibodies or molecules recognizing the same antigen or a different epitope, isoform, subunit, chain, glycosylation or phosphorylation form or an allelic variant of the same antigen, a member of the same complex, or an antigen with the same cell distribution is also included in the present invention.

Further in accordance with the present invention, there is provided examples showing how at least two different surface antigens from blood and/or endometrial leukocytes can be used in combinations in a diagnostic test for endometriosis (Tables 1 and 2).

TABLE 1

Levels of sensibility and specificity provided by several examples of endometrial and/or blood marker combinations used as a diagnostic method for endometriosis

| Marker combination | Threshold value[1] | Specificity | Sensibility |
|---|---|---|---|
| Endometrial leukocyte markers | | | |
| 1. | | | |
| CD4+ (<17%)[2] | >67% | 90% | 67% |
| CD8+CD69− (<21%) | | | |
| CD13+CD45RO− (<17.5%) | | | |
| 2. | | | |
| CD4+ (<15.5%) | >60% | 89% | 65% |
| CD8+CD69− (<21%) | | | |
| CD56+CD122− (>19%) | | | |
| CD3+CD45RA− (<35%) | | | |
| CD13+CD45RO− (<17.5%) | | | |
| 3. | | | |
| CD4+ (<17%) | >67% | 88% | 65% |
| CD8+CD69− (<21%) | | | |
| CD13−CD122+ (>28%) | | | |
| CD13+CD45RO− (<17.5%) | | | |
| 4. | | | |
| CD4+ (<17%) | >67% | 89% | 63% |
| CD8+CD69− (<21%) | | | |
| CD14+CD13−CD16b− (>14.5%) | | | |
| 5. | | | |
| CD3+CD16− (<40%) | >55% | 84% | 62% |
| CD13+CD45RO− (<13.5%) | | | |
| CD3+ (<40%) | | | |
| CD8+ (<20%) | | | |
| CD3+CD69+ (<15%) | | | |
| 6. | | | |
| CD3+ (<40%) | >65% | 84% | 63% |
| CD3+CD8+ (<16%) | | | |
| CD13+CD45RO− (<17.5%) | | | |
| CD3−CD20− (>56%) | | | |
| 7. | | | |
| CD3+CD8+ (<16%) | >65% | 81% | 65% |
| CD13+CD45RO− (<17.5%) | | | |
| CD3+CD5+ (<37%) | | | |
| CD3+CD122− (<42.5%) | | | |
| CD3−C020− (>56%) | | | |
| CD3+CD45RO− (<30%) | | | |
| 8. | | | |
| CD3+CD8+ (<16%) | >60% | 82% | 64% |
| CD13+CD45RO− (<17.5%) | | | |
| CD3+CD5+ (<37%) | | | |
| CD3+CD122− (<42.5%) | | | |
| 9. | | | |
| CD3+CD20−CD5− (>7.7%) | >60% | 81% | 66% |
| CD4+CD13− (<20.5%) | | | |
| CD56−CD122− (<47%) | | | |
| 10. | | | |
| CD3+CD8+ (<16%) | >60% | 80% | 65% |
| CD13+CD45RO− (<17.5%) | | | |
| CD4+CD45RA− (<16%) | | | |
| CD3+CD45RO− (<30%) | | | |
| 11. | | | |
| CD3+ (<40%) | >35% | 79% | 67% |
| CD8+CD69− (<18%) | | | |
| CD3−CD4−CD45RO+ (>56%) | | | |
| Ratio CD13+/CD3+ (>0.675%) | | | |
| CD13+CD45RO− (<21%) | | | |
| 12. | | | |
| CD3+CD8+ (<16%) | >70% | 81% | 61% |
| CD13+CD45RO− (<17.5%) | | | |
| CD3−CD5− (>54%) | | | |
| CD20−CD5+ (<44%) | | | |
| 13. | | | |
| CD8+ (<20%)[2] | >51% | 81% | 60% |
| CD5+ (<37%) | | | |
| CD3−CD20− (>58%) | | | |
| CD3−HLADR− (>54.5%) | | | |
| 14. | | | |
| CD3+CD8+ (<16%) | >60% | 81% | 60% |

TABLE 1-continued

Levels of sensibility and specificity provided by several examples of endometrial and/or blood marker combinations used as a diagnostic method for endometriosis

| Marker combination | Threshold value[1] | Specificity | Sensibility |
|---|---|---|---|
| CD13+CD45RO− (<17.5%) CD5+ (<40%) | | | |
| 15. | | | |
| CD4+ (<17%) CD13−CD122+ (>28%) CD8+CD69− (<19.5%) CD3+CD45RA− (<37%) | >50% | 76% | 71% |
| 16. | | | |
| CD4+ (<15.5%) CD8+CD69− (<21%) CD13−CD122+ (>28%) CD3+CD45RA− (<35%) CD13+CD45RO− (<17.5%) | >35% | 71% | 78% |
| 17. | | | |
| CD4+ (<15.5%) CD8+CD69− (<21%) CD56−CD122− (<47%) CD3+CD45RA− (<35%) CD13+CD45RO− (<17.5%) | >40% | 70% | 78% |
| 18. | | | |
| CD3+ (<40%) CD4+ (<17%) CD3+CD8+ (<16%) CD13+CD45RO− (<21%) CD3+CD5+ (<37%) | >35% | 72% | 76% |
| 19. | | | |
| CD3+ (<40%) CD4+ (<17%) CD3+CD8+ (<16%) CD13+CD45RO− (<21%) | >40% | 74% | 74% |
| 20. | | | |
| CD3+ (<40%) CD3+CD8+ (<16%) CD13+CD45RO− (<21%) | >40% | 75% | 73% |
| 21. | | | |
| CD3+ (<40%) CD5+ (<40%) CD3+CD5+ (<37%) CD69+ (<33%) CD4−CD69+ (<35%) | >25% | 71% | 69% |
| 22. | | | |
| CD3+ (<40%) CD3+CD8+ (<13.5%) CD13+CD45RO− (<17.5%) | >30% | 68% | 83% |
| 23. | | | |
| CD3+ (<40%) CD3+CD8+ (<16%) CD13+CD45RO− (<17.5%) | >30% | 61% | 86% |
| 24. | | | |
| CD3+ (<40%) CD3+CD8+ (<16%) CD13+CD45RO− (<17.5%) CD3−CD20− (>58%) CD56−CD16− (<46%) | >22% | 62% | 80% |
| 25. | | | |
| CD3+CD16− (<47.5%) CD3−CD4−CD45RO+ (>31.5%) CD3+ (<40%) CD8+ (<20%) CD3+CD69+ (<15%) CD13+CD45RO− (<17.5%) | >45% | 66% | 79% |
| 26. | | | |
| CD3+ (<40%) CD3−CD45RO+ (>15%) Ratio CD13+/CD3+ (>0.675%) CD3+CD8+ (<16%) CD8+CD69− (<21%) | >40% | 66% | 75% |
| 27. | | | |
| CD3+CD20−CD5− (>7.7%) CD4+CD13− (<20.5%) CD56−CD122− (<47%) | >45% | 61% | 80% |
| CD4+CD45RO− (<16%) | | | |
| 28. | | | |
| CD3+ (<40%) CD3+CD8+ (<16%) CD13+CD45RO− (<17.5%) CD3−CD20− (>58%) | >20% | 61% | 86% |
| 29. | | | |
| CD13+CD45RO− (<17.5%) CD4+CD45RA− (<16%) CD3+CD122− (42.5%) CD8+CD69− (<21%) | >70% | 90% | 54% |
| 30. | | | |
| CD3+CD8+ (<16%) CD13+CD45RO− (<17.5%) CD4+CD45RA− (<16%) CD3+CD45RO− (<30%) CD3−CD5− (>54%) | >70% | 84% | 60% |
| Blood leukocyte markers | | | |
| 31. | | | |
| CD3−CD5+ (>14.5%) CD3−CD45RA− (>14.5%) CD3−CD44+ (>13%) CD13+ (>17.5%) CD3−CD57−CD44 (<41.3%) | >55% | 66% | 60% |
| 32. | | | |
| CD3−CD45RA (>17%) CD20−CD44+ (>17%) CD20−HLADR+ (>20%) CD3−CD4−CD44+ (>40.5%) CD36−HLADR+ (<5.6%) | >22% | 61% | 64% |
| 33. | | | |
| CD3−CD45RA− (>14.5%) CD3−CD45RO+ (>19%) CD20−HLADR+ (>14.5%) | >40% | 62% | 64% |
| Blood (in italics) and endometrial leukocyte markers | | | |
| 34. | | | |
| *CD57+ (>10%)* *CD14+ (>10%)* *CD3−CD69+ (>17.5%)* CD3+ (<40%) CD4+ (<15.5%) CD3+CD8+HLADR− (<35%) | >50% | 76% | 72% |
| 35. | | | |
| *CD3−CD69+ (>17.5%)* CD3+ (<40%) CD4+ (<15.5%) CD3+CD8+HLADR− (<35%) | >33% | 70% | 79% |
| 36. | | | |
| *CD4−CD36+ (>14.4%)* *CD3−CD69+ (>17.5%)* CD8+ (<20%) CD13+ (>29%) CD3+ (<40%) CD16+ (>27%) CD69+ (<33%) CD5+ (<40%) | >43% | 70% | 74% |
| 37. | | | |
| *CD3−CD45RA− (>14.5%)* *CD3−CD45RO+ (>19%)* *CD20−HLADR+ (>14.5%)* *CD14+CD44+ (>15%)* CD8+ (<20%) CD5+ (<37%) CD3−CD20− (>58%) CD3−HLADR− (>54.5%) | >50% | 73% | 71% |

[1] Value above which a diagnosis of endometriosis is given.
[2] Cutoff point established for each individual marker.

TABLE 2

Examples of logistic regression models provided by endometrial or blood leukocyte markers for the identification of patients with endometriosis

| Marker combination | B value | Threshold value[1] | Specificity | Sensibility | Number of sample tested |
|---|---|---|---|---|---|
| Endometrial leukocyte markers | | | | | |
| Combination no. 1 | | | | | |
| 1. CD3+ (<40%)[2] | −7.9747 | >.55 | 83% | 79% | 41 |
| 2. CD3−CD5− (>60%) | 7.2921 | | | | |
| 3. CD13+CD45RO− (<17.5%) | −0.1410 −1.6259 | | | | |
| 4. CD3−CD20− (>58%) | 9.5142 | | | | |
| Interaction of 1 to 4 | | | | | |
| Constant = 2.0516 | | | | | |
| Combination no. 2 | | | | | |
| 1. CD3+ (<40%) | −6.7753 | >.55 | 74% | 73% | 67 |
| 2. CD3−CD5− (>60%) | 5.8240 | | | | |
| 3. CD13+CD45RO− (<17.5%) | −1.9298 −0.0262 | | | | |
| Interaction 1 to 4 | 2.8385 | | | | |
| Constant = 2.7910 | | | | | |
| Combination no. 3 | | | | | |
| 1. CD3+CD8+ (<16%) | −0.1308 | >.50 | 84% | 72% | 51 |
| 2. CD13+CD45RO− (<17.5%) | −2.6688 −1.1778 | | | | |
| 3. CD3+CD5+ (<37%) | | | | | |
| Constant = 3.1417 | | | | | |
| Combination no. 4 | | | | | |
| 1. CD3+ (<40%) | −1.6965 | >.50 | 78% | 75% | 81 |
| 2. Length of menstruation (>7 days) | −1.8160 −1.9656 | | | | |
| 3. CD13+CD20− (<21%) | 10.3064 | | | | |
| 4. Pelvic pain[3] | | | | | |
| Constant = 3.1984 | | | | | |
| Blood leukocyte markers | | | | | |
| Combination no. 1 | | | | | |
| 1. CD14+CD44+ (>15%) | 0.9298 | >0.55 | 80% | 70% | 140 |
| 2. CD57+ (>10%) | 0.7423 | | | | |
| 3. CD3−CD45RA− (>12%) | −0.8147 | | | | |
| 4. CD14+ (>10%) | 0.8629 | | | | |
| Combination no. 2 | | | | | |
| 1. CD14+ (>10%) | 10.5891 | >.50 | 65% | 71% | 125 |
| 2. CD57+ (>10%) | 0.7326 | | | | |
| 3. CD3+CD69+ (>17.5%) | 0.6899 | | | | |
| 4. CD3+HLADR+ (<4%) | 1.2004 | | | | |
| 5. CD3−CD45RA− (>12%) | −0.1137 | | | | |
| Constant = −1.2062 | | | | | |
| Combination no. 3 | | | | | |
| 1. CD14+ (>10%) | 1.1994 | >.55 | 76% | 75% | 142 |
| 2. CD57+ (>10%) | 0.8080 | | | | |
| 3. CD3+HLADR− (<4%) | 1.3593 | | | | |
| 4. CD3−CD45RA− (>12%) | −0.63 | | | | |
| 5. Pelvic pain | 2.1506 | | | | |
| 6. Length of menstruation (>7 d) | .7489 | | | | |
| Constant = −1.771 | | | | | |
| Combination no. 4 | | | | | |
| 1. CD14+ (>10%) | .9727 | >.50 | 71% | 78% | 141 |
| 2. CD57+ (>10%) | .4489 | | | | |

TABLE 2-continued

Examples of logistic regression models provided by
endometrial or blood leukocyte markers for the
identification of patients with endometriosis

| Marker combination | B value | Threshold value[1] | Specificity | Sensibility | Number of sample tested |
|---|---|---|---|---|---|
| 3. CD3+CD69+ (>17.5%) | .8129 1.3368 | | | | |
| 4. CD3+HLADR− (<4%) | −0.8805 | | | | |
| 5. CD3−CD45RA− (>12%) | 2.1574 | | | | |
| 6. Pelvic pain | 1.5164 | | | | |
| 7. Age (>40) | | | | | |
| Constant = −1.7686 | | | | | |

[1]Value above which a diagnosis of endometriosis is given.
[2]Cutoff point established for each individual marker.
[3]presence of pain at any time other than menstruation and intercourse The predictive models for endometriosis were established according to the following equation:

$$P(r) = \frac{e^{c+B1*(marker1)+B2*(marker2)+\ldots Bn*(marker\ n)}}{1 + e^{c+B1*(marker1)+B2*(marker2)+\ldots Bn*(marker\ n)}}$$

Where: P(r)=probability of having endometriosis;

c=constant established for a particular combination;

B=coefficient of regression; and n=total number of markers in the combination.

In the present invention, a series of endometrial and peripheral blood leukocyte subpopulations for which proportions were modulated in patients with endometriosis (stage I–IV;I–II or III–IV) compared with those of normal controls, have been identified. The novelty of the present invention is to use these leukocyte subpopulations, either alone or in combination, as markers for the diagnosis of endometriosis. Moreover, risk factors for endometriosis identified amongst personal information and menstrual characteristics were shown to be of significant value when used in combination with blood or endometrial leukocyte subsets in a predictive test for endometriosis.

Two methods were used for the combination of markers.

Method 1

A cutoff point is established for the proportion of each leukocyte markers in order to obtain the best discrimination between patients with endometriosis and controls. The proportion obtained for each marker is compared to the cutoff point. A positive test result gives a score of 1, whereas a negative test result gives a score of 0. The diagnostic value is obtained by adding the scores of all the markers of a particular combination and converting it in percentage. The final diagnostic value is then compared to a threshold value that was established to provide the best levels of sensibility and specificity. A positive diagnosis of endometriosis is given when the final diagnostic value exceeds the threshold value established for a particular combination of markers. On the opposite, a negative diagnosis of endometriosis is given when the final diagnostic value is lower than the threshold value (see FIG. 1).

Method 2

A predictive model for endometriosis is established by including each marker of a particular combination in the following logistic regression equation:

$$P(r) = \frac{e^{c+B1*(marker1)+B2*(marker2)+\ldots Bn*(marker\ n)}}{1 + e^{c+B1*(marker1)+B2*(marker2)+\ldots Bn*(marker\ n)}}$$

Where:

P(r)=probability of having endometriosis;

c=constant established for a particular combination;

B=coefficient of regression; and n=total number of markers in the combination.

The probability of having endometriosis (P(r)) is then compared to a threshold value that provides the best discriminative value. A positive diagnosis of endometriosis is given when the P(r) value exceeds the threshold value established for a particular combination of markers. Alternatively, a negative diagnosis of endometriosis is given when the P(r) value is lower than the threshold value.

In the present invention, there is reported a series of 102 endometrial CD45+ leukocyte populations and 93 blood mononuclear CD45+ leukocyte populations which were shown by flow cytometric analysis to be modulated in patients with endometriosis compared with normal controls and, thus are candidate markers for the diagnosis of endometriosis (Tables 3, 4, 5, and 6). An innovative feature of the present invention is to use these markers in combination to increase their level of sensibility and specificity in the diagnostic test.

TABLE 3

Endometrial leukocyte populations proposed as good predictive markers for the identification of patients with endometriosis

| Leukocyte Subsets | Mean proportion (% ± s.d.) of leukocyte subsets | | $P^1$ | Number of samples tested | | area under ROC curve$^2$ | $P^3$ | Cutoff point | Specificity | Sensitivity | Odds ratio | $(CI)^4$ |
|---|---|---|---|---|---|---|---|---|---|---|---|---|
| | Controls | Endo stage I–IV | | Control | Endo | | | | | | | |
| CD3+ | 47.7 ± 12.3 | 38.7 ± 12.6 | $3.37 \times 10^{-5}$ | 58 | 88 | 0.703 | $3.3 \times 10^{-5}$ | <40 | 84 | 55 | 6.5 | (2.9–14.9) |
| CD4+ | 18.3 ± 5.6 | 15.7 ± 5.9 | 0.008 | 55 | 88 | 0.632 | 0.008 | <17 | 63 | 63 | 3.0 | (1.5–6.2) |
| | | | | | | | | <15.5 | 72 | 52 | 2.9 | (1.4–6.0) |
| CD5+ | 45.1 ± 11.6 | 36.3 ± 12.3 | $1.6 \times 10^{-4}$ | 46 | 74 | 0.702 | 0.0002 | <37 | 80 | 53 | 4.2 | (1.8–9.7) |
| | | | | | | | | <40 | 73 | 58 | 3.9 | (1.7–8.8) |
| CD8+ | 24.3 ± 8.5 | 18.5 ± 8.6 | $1.4 \times 10^{-4}$ | 54 | 87 | 0.688 | 0.00019 | <20 | 74 | 62 | 4.8 | (2.3–10.2) |
| CD3+CD4+ | 17.2 ± 5.5 | 14.4 ± 5.7 | 0.004 | 55 | 88 | 0.641 | 0.004 | <15 | 67 | 57 | 2.7 | (1.3–5.5) |
| CD3+CD4− | 29.9 ± 9.6 | 23.6 ± 9.1 | $1.2 \times 10^{-4}$ | 55 | 88 | 0.687 | 0.00017 | <24 | 80 | 52 | 4.4 | (2.0–9.6) |
| CD3−CD4− | 51.1 ± 14.2 | 60.8 ± 12.6 | $4.1 \times 10^{-5}$ | 55 | 88 | 0.698 | $6.9 \times 10^{-5}$ | >61 | 83 | 50 | 5.1 | (2.2–11.7) |
| CD3+CD8+ | 18.9 ± 7.5 | 13.7 ± 7.7 | $1.1 \times 10^{-4}$ | 54 | 84 | 0.714 | $2.3 \times 10^{-5}$ | <16 | 70 | 70 | 5.6 | (2.6–11.8) |
| | | | | | | | | <13.5 | 81 | 54 | 5.3 | (2.3–11.9) |
| CD3+CD8− | 26.1 ± 7.8 | 23.1 ± 7.1 | 0.022 | 54 | 84 | 0.609 | | <23.5 | 68 | 51 | 2.2 | (1.1–4.7) |
| CD3−CD8− | 49.6 ± 12.0 | 58.2 ± 13.0 | $1.3 \times 10^{-4}$ | 54 | 84 | 0.688 | $1.9 \times 10^{-4}$ | >53.5 | 70 | 63 | 4.0 | (1.9–8.5) |
| CD3+CD69+ | 20.4 ± 9.6 | 15.5 ± 8.0 | 0.003 | 44 | 76 | 0.642 | 0.010 | <15 | 67 | 53 | 2.4 | (1.1–5.2) |
| CD3+CD122− | 41.4 ± 10.0 | 34.4 ± 12.4 | 0.011 | 29 | 53 | 0.669 | 0.012 | <42.5 | 64 | 76 | 2.9 | (1.1–7.5) |
| CD3+HLADR− | 38.1 ± 10.3 | 30.6 ± 12.3 | $2.8 \times 10^{-4}$ | 51 | 80 | 0.681 | 0.0005 | <35 | 72 | 63 | 4.0 | (1.8–8.5) |
| CD3−HLADR− | 46.4 ± 13.0 | 55.6 ± 13.5 | $1.9 \times 10^{-4}$ | 51 | 80 | 0.693 | 0.0002 | >54.5 | 80 | 51 | 4.1 | (1.8–9.3) |
| CD3+CD45RA+ | 7.4 ± 4.7 | 5.7 ± 3.0 | 0.018 | 56 | 85 | 0.608 | 0.030 | <4.9 | 77 | 40 | 2.2 | (1.0–4.7) |
| CD3+CD45RA− | 40.3 ± 11.2 | 32.7 ± 12.0 | $2.5 \times 10^{-4}$ | 56 | 85 | 0.684 | 0.0002 | <37 | 69 | 66 | 4.7 | (2.2–9.7) |
| | | | | | | | | <35 | 73 | 60 | 4.1 | (1.9–8.5) |
| CD3−CD45RA− | 31.4 ± 12.7 | 39.6 ± 13.4 | $4.2 \times 10^{-4}$ | 56 | 85 | 0.667 | $8.2 \times 10^{-4}$ | >32 | 51 | 69 | 2.3 | (1.1–4.6) |
| CD3+CD45RO− | 31.0 ± 11.1 | 25.0 ± 9.8 | 0.002 | 50 | 73 | 0.661 | 0.002 | <28 | 65 | 62 | 3.1 | (1.4–6.6) |
| | | | | | | | | <30 | 55 | 70 | 2.7 | (1.3–5.7) |
| CD3+CD16− | 45.5 ± 12.1 | 37.2 ± 13.1 | $2.1 \times 10^{-4}$ | 57 | 83 | 0.680 | 0.0003 | <38 | 80 | 49 | 4.5 | (2.0–9.9) |
| | | | | | | | | <40 | 75 | 58 | 4.2 | (2.0–8.9) |
| | | | | | | | | <47.5 | 40 | 80 | 2.6 | (1.2–5.6) |
| CD3+CD56− | 46.5 ± 12.2 | 38.5 ± 12.8 | $3.2 \times 10^{-4}$ | 56 | 83 | 0.674 | 0.00053 | <40 | 78 | 55 | 4.6 | (2.1–9.9) |
| CD3+CD5+ | 41.9 ± 11.4 | 33.2 ± 12.3 | $2.1 \times 10^{-4}$ | 45 | 74 | 0.695 | 0.00036 | <37 | 77 | 61 | 4.7 | (2.1–10.9) |
| CD3−CD5− | 50.6 ± 12.0 | 59.0 ± 12.9 | 0.001 | 45 | 74 | 0.690 | 0.00052 | >60 | 82 | 51 | 4.6 | (1.9–11.2) |
| | | | | | | | | >54 | 66 | 66 | 4.3 | (1.9–9.6) |
| CD4+CD69− | 16.4 ± 4.8 | 13.8 ± 5.1 | 0.012 | 37 | 72 | 0.648 | 0.012 | <14 | 78 | 53 | 4.1 | (1.6–10.1) |
| CD4+CD45RA− | 16.7 ± 5.3 | 14.2 ± 5.7 | 0.010 | 54 | 85 | 0.632 | 0.009 | <16 | 62 | 66 | 3.3 | (1.6–6.7) |
| CD8+CD69− | 24.0 ± 7.9 | 18.9 ± 8.3 | 0.007 | 30 | 59 | 0.687 | 0.004 | <18 | 83 | 53 | 5.9 | (1.9–17.6) |
| | | | | | | | | <19.5 | 76 | 59 | 5.1 | (1.9–13.9) |
| | | | | | | | | <21 | 65 | 68 | 4.2 | (1.6–10.7) |
| CD8+HLADR− | 23.3 ± 7.7 | 18.1 ± 8.5 | 0.001 | 49 | 79 | 0.673 | 0.001 | <18 | 77 | 54 | 4.1 | (1.8–9.2) |
| CD8−HLADR− | 61.6 ± 9.5 | 68.1 ± 9.5 | $2.2 \times 10^{-4}$ | 49 | 79 | 0.675 | 0.0009 | >61.5 | 52 | 77 | 3.8 | (1.7–8.3) |
| CD13−CD122+ | 27.0 ± 9.8 | 33.6 ± 18.7 | 0.031 | 32 | 58 | 0.605 | | >28 | 64 | 59 | 2.5 | (1.0–6.2) |
| CD13−CD122− | 47.1 ± 14.4 | 40.4 ± 15.0 | 0.043 | 32 | 58 | 0.635 | 0.035 | <46 | 58 | 64 | 2.6 | (1.1–6.2) |
| CD20−CD5+ | 44.6 ± 12.0 | 36.4 ± 12.6 | 0.001 | 41 | 66 | 0.681 | 0.002 | <41 | 60 | 62 | 2.6 | (1.2–5.7) |
| | | | | | | | | <44 | 57 | 71 | 3.5 | (1.5–7.9) |
| CD20−CD5− | 52.0 ± 12.8 | 60.9 ± 12.9 | 0.001 | 41 | 66 | 0.692 | 0.0009 | >60 | 77 | 50 | 3.6 | (1.5–8.6) |
| CD56−CD16+ | 22.0 ± 12.2 | 27.0 ± 16.6 | 0.044 | 56 | 84 | 0.571 | | | | | | |
| CD56−CD16− | 51.6 ± 12.2 | 42.8 ± 13.5 | $1.2 \times 10^{-4}$ | 56 | 84 | 0.687 | $1.8 \times 10^{-4}$ | <46 | 71 | 57 | 3.3 | (1.6–6.7) |
| ratio CD3+/CD45RO+ | 1.5 ± 1.0 | 1.2 ± 0.7 | 0.020 | 51 | 80 | 0.626 | 0.015 | | | | | |
| CD14+CD13− | 1.4 ± 0.9 | 2.3 ± 1.8 | 0.041 | 21 | 36 | 0.639 | | | | | | |
| CD3+CD20− | 44.4 ± 11.2 | 36.9 ± 13.5 | 0.024 | 24 | 45 | 0.667 | 0.023 | <40 | 78 | 58 | 4.1 | (1.4–12.3) |
| CD3−CD20− | 52.3 ± 11.5 | 61.0 ± 14.9 | 0.016 | 24 | 45 | 0.669 | 0.022 | >58 | 83 | 53 | 6.2 | (1.8–21.2) |
| | | | | | | | | >56 | 70 | 60 | 4.5 | (1.4–13.5) |
| CD3−CD4−CD45RA+ | 40.1 ± 13.7 | 34.9 ± 15.1 | 0.046 | 51 | 79 | 0.618 | 0.023 | | | | | |
| CD3−CD4−CD45RA− | 57.9 ± 14.1 | 63.3 ± 15.2 | 0.042 | 51 | 79 | 0.620 | 0.021 | | | | | |
| CD3+CD8+CD69− | 40.4 ± 10.2 | 35.1 ± 11.7 | 0.039 | 29 | 56 | 0.635 | 0.042 | <34.5 | 75 | 52 | 3.4 | (1.2–9.2) |
| CD3+CD8+HLADR− | 39.5 ± 9.2 | 33.6 ± 11.5 | 0.003 | 48 | 74 | 0.665 | 0.002 | <35 | 72 | 55 | 3.5 | (1.6–7.7) |
| CD3+CD8−HLADR− | 43.1 ± 7.5 | 46.3 ± 10.9 | | 48 | 74 | 0.603 | | >47 | 69 | 50 | 2.2 | (1.0–4.7) |
| CD3−CD8−HLADR− | 76.7 ± 8.9 | 80.3 ± 7.9 | 0.021 | 48 | 74 | 0.597 | | | | | | |
| CD14+CD13−CD16b− | 19.8 ± 16.4 | 33.4 ± 22.9 | 0.026 | 19 | 36 | 0.703 | 0.014 | >23 | 68 | 69 | 4.9 | (1.4–16.3) |
| | | | | | | | | >14.5 | 53 | 83 | 4.6 | (1.4–15.6) |
| CD4+CD14− | 20.7 ± 7.8 | 14.8 ± 5.8 | 0.014 | 14 | 23 | 0.738 | 0.017 | <16.6 | 79 | 65 | 6.9 | (1.5–32.0) |
| CD4−CD14− | 75.7 ± 8.1 | 81.0 ± 5.7 | 0.025 | 14 | 23 | 0.711 | 0.033 | >76 | 57 | 83 | 6.3 | (1.4–28.7) |
| CD4+HLADR− | 16.0 ± 5.7 | 12.3 ± 4.1 | 0.018 | 14 | 30 | 0.715 | 0.023 | <17 | 57 | 87 | 8.7 | (1.9–38.6) |
| CD13−CD69+ | 54.2 ± 14.3 | 42.3 ± 18.2 | 0.039 | 14 | 30 | 0.705 | 0.030 | <51 | 71 | 70 | 5.8 | (1.4–23.6) |
| CD13+CD45RO− | 22.1 ± 8.8 | 15.5 ± 10.7 | 0.009 | 25 | 54 | 0.746 | $4.6 \times 10^{-4}$ | <17.5 | 76 | 70 | 7.5 | (2.5–22.3) |
| | | | | | | | | <21 | 52 | 80 | 4.2 | (1.5–11.8) |
| CD56−CD122− | 49.0 ± 12.2 | 42.8 ± 15.8 | | 29 | 51 | 0.631 | | <47 | 65 | 69 | 3.6 | (1.4–9.3) |
| CD3+CD69− | 26.4 ± 7.0 | 23.3 ± 8.4 | 0.036 | 44 | 76 | 0.612 | 0.041 | <27 | 57 | 67 | 2.2 | (1.0–4.8) |
| CD4+CD45RO− | 14.9 ± 5.3 | 13.0 ± 6.2 | | 47 | 74 | 0.615 | 0.034 | <16 | 51 | 72 | 2.6 | (1.2–5.6) |
| CD56+CD122+ | 3.5 ± 2.2 | 2.6 ± 1.7 | | 29 | 51 | 0.651 | 0.025 | <3.0 | 55 | 73 | 3.3 | (1.3–8.5) |
| CD3−CD56+CD16+ | 8.2 ± 3.8 | 6.8 ± 4.0 | 0.049 | 53 | 78 | 0.615 | 0.026 | <6.5 | 72 | 55 | 3.0 | (1.4–6.2) |
| CD3−CD56+CD122+ | 3.6 ± 2.0 | 2.6 ± 1.8 | 0.033 | 27 | 49 | 0.638 | 0.048 | <2.7 | 63 | 65 | 3.2 | (1.2–8.5) |

TABLE 3-continued

Endometrial leukocyte populations proposed as good predictive markers for the identification of patients with endometriosis

| Leukocyte Subsets | Mean proportion (% ± s.d.) of leukocyte subsets | | $P^1$ | Number of samples tested | | area under ROC curve[2] | $P^3$ | Cutoff point | Specificity | Sensitivity | Odds ratio | (CI)[4] |
|---|---|---|---|---|---|---|---|---|---|---|---|---|
| | Controls | Endo stage I–IV | | Control | Endo | | | | | | | |
| CD14+CD13+ | 3.8 ± 1.9 | 3.0 ± 2.6 | | 21 | 36 | 0.672 | 0.032 | <2.3 | 81 | 53 | 4.8 | (1.3–16.9) |
| CD3+CD20−CD5+ | 93.0 ± 2.7 | 88.0 ± 13.8 | | 24 | 40 | 0.659 | 0.034 | <91.5 | 79 | 55 | 4.6 | (1.4–14.9) |
| CD4−CD13+CD16+ | 31.0 ± 14.0 | 22.4 ± 18.9 | | 16 | 36 | 0.699 | 0.023 | | | | | |
| CD69+ | 41.8 ± 12.9 | 38.8 ± 17.8 | | 43 | 78 | 0.557 | | <33 | 81 | 41 | 3.0 | (1.2–7.4) |
| ratio CD13+/CD3+ | 0.56 ± 0.54 | 0.78 ± 0.71 | | 46 | 78 | 0.596 | | >0.68 | 80 | 40 | 2.6 | (1.1–6.1) |
| CD3−CD20−CD5− | 88.0 ± 6.9 | 90.7 ± 5.2 | | 24 | 40 | 0.598 | | >84 | 37 | 90 | 5.4 | (1.4–20.3) |
| CD3+CD20−CD5− | 5.1 ± 2.3 | 9.5 ± 13.6 | | 24 | 40 | 0.683 | 0.015 | >7.7 | 87 | 50 | 9.9 | (2.1–48.1) |
| CD4+CD13− | 17.5 ± 6.9 | 15.8 ± 5.4 | | 36 | 63 | 0.594 | | <20.5 | 42 | 86 | 4.3 | (1.6–11.3) |
| CD3+CD44− | 41.7 ± 12.0 | 38.3 ± 13.6 | | 31 | 56 | 0.596 | | <37.8 | 74 | 50 | 2.9 | (1.1–7.5) |
| CD56+ | 26.2 ± 12.5 | 30.2 ± 17.2 | | 57 | 87 | 0.562 | | >32 | 81 | 41 | 2.9 | (1.3–6.5) |
| CD13−CD45RO+ | 21.4 ± 8.7 | 26.3 ± 11.3 | | 25 | 54 | 0.625 | | >28 | 80 | 45 | 3.2 | (1.0–9.8) |
| CD56+CD69− | 19.6 ± 12.9 | 24.3 ± 14.3 | | 33 | 53 | 0.610 | | >26 | 85 | 40 | 3.4 | (1.1–10.2) |
| CD13−CD16+ | 8.0 ± 7.5 | 6.7 ± 3.3 | | 39 | 71 | 0.562 | | <6 | 72 | 51 | 2.6 | (1.1–6.1) |
| CD56+CD122− | 21.8 ± 11.8 | 28.7 ± 17.3 | | 29 | 51 | 0.621 | | >19 | 59 | 71 | 3.1 | (1.2–7.9) |
| | | | | | | | | >18 | 55 | 72 | 3.3 | (1.3–8.5) |
| CD3+CD4−CD69+ | 37.2 ± 10.0 | 34.0 ± 13.8 | | 34 | 66 | 0.572 | | <33.5 | 73 | 49 | 2.6 | (1.1–6.4) |
| CD4−CD13−CD16+ | 8.5 ± 3.6 | 8.7 ± 10.8 | | 16 | 36 | 0.642 | | <7.1 | 75 | 58 | 4.2 | (1.1–15.6) |
| CD4−CD13−CD16− | 54.5 ± 13.0 | 62.2 ± 21.4 | | 16 | 36 | 0.655 | | >65 | 81 | 56 | 5.4 | (1.3–22.3) |
| CD14+CD13+CD16b+ | 11.0 ± 12.5 | 6.5 ± 6.2 | | 19 | 36 | 0.616 | | <16 | 32 | 94 | 7.8 | (1.4–43.9) |
| CD4−CD69− | 40.7 ± 12.9 | 46.4 ± 18.6 | | 37 | 72 | 0.593 | | >47 | 76 | 47 | 2.8 | (1.2–6.7) |
| CD3−CD45RO+ | 23.0 ± 12.5 | 27.1 ± 16.3 | | 50 | 73 | 0.556 | | >15 | 34 | 80 | | |
| CD4−CD69+ | 39.3 ± 11.8 | 37.7 ± 18.0 | | 37 | 72 | 0.462 | | <35 | 68 | 46 | | |
| CD3−CD4−CD45RO+ | 41.3 ± 18.1 | 43.4 ± 20.9 | | 43 | 72 | 0.530 | | >31.5 | 33 | 71 | | |
| | | | | | | | | >56 | 81 | 28 | | |

[1]P value (when ≤0.05) obtained in a student "t" test when mean proportion found in patients with endometriosis stage I–IV was compared to normal controls.
[2]Discriminative value of each marker established by area under ROC curve.
[3]P value (when ≤0.05), significance of area under ROC curve.
[4]Confidence interval for odds ratio.

TABLE 4

Peripheral blood leukocyte populations proposed as good predictive markers for the identification of patients with endometriosis

| Leukocyte Subsets | Mean proportion (% ± s.d.) of leukocyte subsets | | $P^1$ | Number of samples tested | | area under curve[2] | $P^3$ | Cutoff point | Specificity | Sensitivity | Odds ratio | (CI)[4] |
|---|---|---|---|---|---|---|---|---|---|---|---|---|
| | Control | Endo. Stage I–IV | | Control | Endo. Stage I–IV | | | | | | | |
| CD3+ | 66.6 ± 8.5 | 64.5 ± 8.7 | 0.032 | 132 | 172 | 0.570 | 0.037 | | | | | |
| CD8+ | 17.3 ± 5.2 | 16.4 ± 4.8 | | 129 | 172 | 0.549 | | <18.9 | 33 | 77 | 1.7 | (1.0–2.8) |
| CD13+ | 16.0 ± 6.0 | 17.6 ± 6.5 | 0.039 | 122 | 155 | 0.575 | 0.032 | >17.5 | 63 | 51 | 1.8 | (1.1–2.9) |
| CD14+ | 11.8 ± 4.9 | 13.4 ± 6.0 | 0.020 | 124 | 167 | 0.575 | 0.029 | >10 | 45 | 71 | 2.0 | (1.3–3.3) |
| CD20+ | 5.7 ± 3.1 | 4.8 ± 2.3 | 0.006 | 124 | 162 | 0.582 | 0.017 | <6 | 39 | 74 | 1.8 | (1.1–3.0) |
| CD36+ | 15.7 ± 6.8 | 17.2 ± 7.3 | | 112 | 140 | 0.560 | | >19 | 77 | 37 | 2.1 | (1.2–3.6) |
| CD44+ | 17.1 ± 5.6 | 19.1 ± 6.5 | 0.009 | 113 | 148 | 0.585 | 0.018 | >18.5 | 61 | 51 | 1.7 | (1.0–2.7) |
| CD57+ | 8.0 ± 3.9 | 9.2 ± 4.9 | 0.023 | 114 | 148 | 0.569 | | >10 | 75 | 39 | 1.8 | (1.1–3.1) |
| CD69+ | 19.4 ± 8.2 | 21.0 ± 7.1 | | 109 | 144 | 0.590 | 0.014 | >21.5 | 71 | 45 | 2.0 | (1.2–3.4) |
| CD122+ | 29.2 ± 8.4 | 31.2 ± 11.7 | | 122 | 166 | 0.567 | | >34 | 74 | 42 | 2.1 | (1.2–3.4) |
| CD3+CD5+ | 66.6 ± 8.5 | 63.7 ± 10.4 | 0.017 | 115 | 146 | 0.586 | 0.017 | <69 | 44 | 70 | 1.8 | (1.1–2.9) |
| CD3+CD45RA− | 39.3 ± 9.5 | 37.2 ± 8.3 | 0.044 | 124 | 168 | 0.583 | 0.015 | <42 | 40 | 72 | 1.7 | (1.1–2.8) |
| CD3+CD56− | 65.3 ± 8.8 | 63.2 ± 8.6 | 0.035 | 126 | 169 | 0.571 | 0.037 | <68 | 42 | 71 | 1.8 | (1.1–2.9) |
| CD3+CD57− | 63.7 ± 8.3 | 60.7 ± 9.7 | 0.009 | 113 | 146 | 0.592 | 0.011 | <67 | 40 | 77 | 2.3 | (1.3–3.9) |
| CD3+CD69− | 60.1 ± 9.6 | 57.9 ± 9.2 | | 107 | 141 | 0.584 | 0.023 | | | | | |
| CD3+CD122− | 62.2 ± 8.4 | 59.6 ± 9.8 | 0.021 | 121 | 164 | 0.578 | 0.024 | <58 | 69 | 42 | 1.6 | (1.0–2.7) |
| CD3+HLADR+ | 3.9 ± 1.4 | 3.5 ± 1.2 | 0.006 | 121 | 154 | 0.601 | 0.004 | <4 | 40 | 77 | 2.2 | (1.3–3.7) |
| CD3−CD5+ | 15.5 ± 5.3 | 18.3 ± 8.4 | 0.003 | 115 | 146 | 0.619 | 0.001 | >14.5 | 50 | 72 | 2.5 | (1.5–4.2) |
| CD3−CD16+ | 23.3 ± 7.9 | 25.4 ± 8.7 | 0.036 | 123 | 166 | 0.572 | 0.037 | | | | | |
| CD3−CD44+ | 13.1 ± 5.3 | 15.6 ± 6.3 | 0.001 | 111 | 143 | 0.615 | 0.002 | >11.5 | 44 | 73 | 2.2 | (1.4–3.7) |

TABLE 4-continued

Peripheral blood leukocyte populations proposed as good predictive markers for the identification of patients with endometriosis

| Leukocyte Subsets | Mean proportion (% ± s.d.) of leukocyte subsets | | | Number of samples tested | | area under curve[2] | P[3] | Cutoff point | Specificity | Sensitivity | Odds ratio | (CI)[4] |
|---|---|---|---|---|---|---|---|---|---|---|---|---|
| | Control | Endo. Stage I–IV | P[1] | Control | Endo. Stage I–IV | | | | | | | |
| CD3–CD57+ | 4.2 ± 2.5 | 5.0 ± 3.1 | 0.023 | 113 | 146 | 0.573 | 0.044 | | | | | |
| CD3–CD69+ | 14.2 ± 5.6 | 16.4 ± 6.5 | 0.006 | 107 | 141 | 0.602 | 0.006 | >17.5 | 75 | 41 | 2.1 | (1.2–3.6) |
| CD3–CD45RO+ | 16.0 ± 5.6 | 18.1 ± 6.8 | 0.006 | 117 | 148 | 0.595 | 0.008 | >19 | 77 | 44 | 2.6 | (1.5–4.5) |
| CD3–CD4– | 31.1 ± 9.5 | 33.3 ± 9.0 | 0.043 | 132 | 171 | 0.566 | 0.050 | | | | | |
| CD3–CD8– | 33.4 ± 9.2 | 35.5 ± 10.0 | | 122 | 166 | 0.568 | 0.050 | | | | | |
| CD3–CD45RA– | 14.2 ± 5.2 | 16.2 ± 6.2 | 0.004 | 124 | 168 | 0.595 | 0.006 | >14.5 | 61 | 60 | 2.3 | (1.4–3.7) |
| CD3–CD56– | 21.6 ± 6.3 | 23.1 ± 7.0 | | 126 | 169 | 0.562 | | >25 | 73 | 39 | 1.7 | (1.0–2.8) |
| CD4–CD13+ | 14.5 ± 6.0 | 16.3 ± 6.8 | 0.030 | 108 | 131 | 0.586 | 0.023 | >16.5 | 69 | 51 | 2.4 | (1.4–4.1) |
| CD4–CD36+ | 13.8 ± 7.4 | 19.0 ± 6.2 | 0.037 | 13 | 21 | 0.771 | 0.009 | >19 | 92 | 62 | 19.5 | (2.1–179.9) |
| CD4–CD69+ | 16.0 ± 6.1 | 18.1 ± 6.5 | 0.021 | 94 | 120 | 0.603 | 0.009 | >19 | 75 | 45 | 2.4 | (1.3–4.3) |
| CD4–CD45RO+ | 23.4 ± 6.7 | 27.0 ± 7.7 | 0.043 | 27 | 50 | 0.620 | | | | | | |
| CD4–CD45RA– | 22.7 ± 6.5 | 24.4 ± 8.3 | | 125 | 168 | 0.562 | | | | | | |
| CD8–CD44+ | 16.8 ± 5.5 | 18.9 ± 6.7 | 0.017 | 88 | 119 | 0.588 | 0.030 | | | | | |
| CD8–CD44– | 66.4 ± 7.0 | 64.4 ± 6.6 | 0.039 | 88 | 119 | 0.584 | 0.040 | <68 | 48 | 70 | 2.1 | (1.2–3.7) |
| CD13+CD44+ | 13.3 ± 5.3 | 15.4 ± 5.9 | 0.006 | 96 | 121 | 0.605 | 0.008 | >11 | 38 | 76 | 1.9 | (1.1–3.4) |
| CD13+HLADR+ | 13.0 ± 5.3 | 14.7 ± 6.1 | 0.024 | 108 | 135 | 0.581 | 0.031 | >15.5 | 71 | 42 | 1.8 | (1.1–3.1) |
| CD13+CD16– | 1.4 ± 0.9 | 3.7 ± 4.6 | 0.005 | 21 | 37 | 0.727 | 0.004 | >2 | 76 | 57 | 4.2 | (1.3–13.9) |
| CD13–HLADR+ | 8.2 ± 3.2 | 7.0 ± 3.0 | 0.005 | 108 | 135 | 0.619 | 0.001 | <8 | 50 | 70 | 2.4 | (1.4–4.0) |
| CD13–CD44– | 79.9 ± 6.2 | 76.9 ± 8.6 | 0.004 | 96 | 121 | 0.606 | 0.007 | <82 | 39 | 76 | 2.0 | (1.1–3.6) |
| CD14+HLADR+ | 11.0 ± 4.6 | 12.7 ± 5.9 | 0.009 | 109 | 147 | 0.587 | 0.017 | >9.5 | 48 | 70 | 2.2 | (1.3–3.6) |
| CD14+CD44+ | 10.7 ± 4.9 | 12.9 ± 5.7 | 0.003 | 85 | 123 | 0.612 | 0.006 | >15 | 85 | 33 | 2.7 | (1.3–5.4) |
| CD14+CD45RO+ | 12.2 ± 4.4 | 14.3 ± 6.1 | 0.004 | 102 | 118 | 0.586 | 0.028 | | | | | |
| CD14+CD16– | 0.7 ± 0.8 | 2.7 ± 5.4 | 0.023 | 23 | 41 | 0.603 | | | | | | |
| CD14+CD122– | 0.4 ± 0.3 | 2.4 ± 5.2 | 0.029 | 14 | 34 | 0.648 | | >0.7 | 86 | 47 | 5.3 | (1.0–27.5) |
| CD14–HLADR+ | 10.3 ± 3.3 | 9.1 ± 2.7 | 0.001 | 109 | 147 | 0.611 | 0.002 | <8.5 | 69 | 47 | 2.0 | (1.2–3.3) |
| CD14–CD44– | 83.5 ± 5.3 | 81.6 ± 6.3 | 0.023 | 85 | 123 | 0.588 | 0.032 | <80 | 79 | 37 | 2.2 | (1.2–4.2) |
| CD20+HLADR+ | 5.2 ± 2.9 | 4.3 ± 2.1 | 0.005 | 106 | 141 | 0.596 | 0.010 | <5.5 | 39 | 75 | 1.9 | (1.1–3.3) |
| CD20+CD44– | 5.0 ± 2.8 | 4.2 ± 2.2 | 0.033 | 95 | 126 | 0.571 | | <4 | 62 | 55 | 2.0 | (1.2–3.4) |
| CD20–CD44+ | 14.4 ± 5.1 | 17.3 ± 6.2 | 0.0004 | 95 | 126 | 0.636 | 0.001 | >17 | 74 | 47 | 2.5 | (1.4–4.4) |
| CD20–CD69+ | 16.4 ± 4.3 | 21.0 ± 6.2 | 0.016 | 14 | 29 | 0.719 | 0.021 | >16 | 57 | 76 | 4.2 | (1.1–16.3) |
| CD20–HLADR+ | 15.4 ± 4.9 | 17.6 ± 6.9 | 0.004 | 106 | 141 | 0.591 | 0.014 | >14.5 | 49 | 70 | 2.2 | (1.3–3.7) |
| CD20–CD44– | 79.5 ± 5.1 | 77.5 ± 6.1 | 0.008 | 95 | 126 | 0.590 | 0.022 | | | | | |
| CD20–CD69– | 79.4 ± 6.7 | 75.3 ± 6.5 | 0.065 | 14 | 29 | 0.711 | 0.027 | <75.6 | 71 | 52 | 11.6 | (2.3–57.0) |
| CD36–HLADR+ | 7.8 ± 3.2 | 6.4 ± 2.0 | 0.0005 | 95 | 121 | 0.629 | 0.001 | <5.6 | 77 | 40 | 2.2 | (1.2–4.0) |
| CD56–CD69+ | 18.1 ± 4.2 | 21.8 ± 6.7 | 0.083 | 13 | 23 | 0.667 | | >20.5 | 85 | 52 | 6.0 | (1.1–33.3) |
| CD56–CD122+ | 19.5 ± 5.7 | 21.4 ± 8.6 | 0.028 | 113 | 154 | 0.578 | 0.030 | >23 | 74 | 40 | 2.0 | (1.2–3.3) |
| CD56–CD69– | 67.9 ± 5.3 | 62.7 ± 9.4 | 0.075 | 13 | 23 | 0.671 | 0.093 | | | | | |
| CD56–CD122– | 67.7 ± 8.3 | 64.7 ± 11.5 | 0.014 | 113 | 154 | 0.586 | 0.017 | <64.5 | 67 | 51 | 2.1 | (1.3–3.5) |
| CD57–CD44– | 74.3 ± 6.9 | 71.7 ± 7.7 | 0.015 | 84 | 117 | 0.602 | 0.014 | <76 | 44 | 71 | 1.9 | (1.1–3.5) |
| CD3+CD57–HLADR+ | 4.3 ± 1.5 | 4.0 ± 1.4 | | 96 | 118 | 0.584 | 0.034 | <3.7 | 72 | 43 | 1.9 | (1.1–3.5) |
| CD3–CD4–CD44+ | 34.4 ± 11.0 | 38.1 ± 12.6 | 0.032 | 88 | 112 | 0.577 | | >40.5 | 69 | 45 | 1.8 | (1.0–3.3) |
| CD3–CD56+CD16– | 1.2 ± 0.6 | 1.4 ± 1.0 | 0.023 | 121 | 163 | 0.553 | | | | | | |
| CD3–CD56–CD122– | 23.4 ± 11.1 | 21.2 ± 11.4 | | 113 | 148 | 0.581 | 0.024 | | | | | |
| CD3–CD57–CD44– | 48.7 ± 10.1 | 44.5 ± 10.3 | 0.004 | 84 | 114 | 0.610 | 0.008 | <41.3 | 80 | 41 | 2.8 | (1.4–5.3) |
| CD14+CD20+CD44– | 0.2 ± 0.2 | 0.1 ± 0.1 | 0.036 | 65 | 75 | 0.613 | 0.037 | | | | | |
| CD14+CD20–CD44+ | 91.8 ± 4.6 | 93.5 ± 3.5 | 0.016 | 65 | 75 | 0.614 | 0.021 | >95 | 75 | 43 | 2.3 | (1.1–4.7) |
| CD14+CD20–CD44– | 5.9 ± 4.5 | 4.6 ± 3.3 | 0.037 | 65 | 75 | 0.604 | 0.035 | <3 | 75 | 43 | 2.3 | (1.1–4.7) |
| CD14–CD13–HLADR+ | 8.7 ± 3.5 | 7.6 ± 2.6 | 0.021 | 77 | 82 | 0.600 | 0.029 | <7 | 71 | 45 | 2.1 | (1.1–4.0) |
| Ratio CD13+/CD3+ | 0.25 ± 0.12 | 0.29 ± 0.14 | 0.025 | 121 | 153 | 0.583 | 0.018 | >0.30 | 71 | 43 | 1.8 | (1.1–3.0) |
| Ratio CD13+CD8+ | 1.04 ± 0.55 | 1.20 ± 0.69 | 0.039 | 114 | 153 | 0.574 | 0.039 | | | | | |
| Ratio CD14+/CD3+ | 0.19 ± 0.10 | 0.22 ± 0.12 | 0.011 | 123 | 165 | 0.575 | 0.028 | >0.14 | 40 | 74 | 1.9 | (1.1–3.1) |
| Ratio CD14+/CD8+ | 0.78 ± 0.47 | 0.91 ± 0.55 | 0.040 | 116 | 164 | 0.574 | 0.036 | | | | | |

[1]P value (when ≦0.05) obtained in a student "t" test when mean proportion of leukocyte subsets was compared between patients with endometriosis (stage I–IV) and normal controls.
[2]Discriminative value of each marker established by area under ROC curve.
[3]P value (when ≦0.05), significance of area under ROC curve.
[4]Confidence interval for odds ratio.

TABLE 5

Endometrial leukocyte populations used as markers to discriminate between patients with endometriosis stage I–II or stage III–IV and normal subjects

| Leukocyte Subsets | Mean proportion (% ± s.d.) of leukocyte subsets | | | | | Number of samples tested | | |
|---|---|---|---|---|---|---|---|---|
| | Controls | Endo stage I–II | P[1] | Endo stage III–IV | P[2] | Control | Endo I–II | Endo III–IV |
| CD3−CD44− | 50.0 ± 12.9 | 50.5 ± 11.9 | | 61.8 ± 16.6 | 0.015 | 31 | 43 | 13 |
| CD3+HLADR+ | 8.3 ± 5.7 | 6.1 ± 2.6 | 0.013 | 7.6 ± 3.3 | | 51 | 57 | 23 |
| CD3+CD45RO+ | 14.9 ± 8.4 | 12.0 ± 5.6 | 0.043 | 13.2 ± 9.5 | | 50 | 50 | 23 |
| CD4+CD13+ | 2.3 ± 1.9 | 2.2 ± 1.7 | | 1.4 ± 1.1 | 0.025 | 36 | 44 | 19 |
| CD13+HLADR+ | 5.7 ± 2.7 | 5.3 ± 2.3 | | 3.6 ± 1.3 | 0.017 | 27 | 37 | 12 |
| CD14−HLADR+ | 14.7 ± 7.5 | 10.2 ± 3.9 | 0.049 | 10.8 ± 5.1 | | 14 | 24 | 4 |
| CD56+HLADR+ | 2.8 ± 1.7 | 1.5 ± 0.7 | 0.011 | 4.6 ± 3.3 | | 16 | 17 | 5 |
| CD56−CD44− | 63.5 ± 13.0 | 63.5 ± 13.4 | | 51.1 ± 20.4 | 0.023 | 30 | 41 | 12 |
| CD3−CD4+CD45RA− | 1.5 ± 0.9 | 1.5 ± 0.9 | | 1.0 ± 0.7 | 0.022 | 51 | 54 | 25 |
| CD3+CD8−HLADR+ | 15.9 ± 8.1 | 15.8 ± 8.6 | | 23.6 ± 12.1 | 0.011 | 48 | 52 | 22 |
| CD3+CD8+HLADR− | 9.5 ± 6.5 | 8.6 ± 6.1 | | 6.1 ± 5.2 | 0.036 | 48 | 52 | 22 |
| CD3+CD56+CD16+ | 3.0 ± 3.4 | 2.9 ± 3.2 | | 6.0 ± 5.7 | 0.027 | 53 | 56 | 22 |
| CD3+CD56−CD16+ | 6.6 ± 7.5 | 7.0 ± 6.2 | | 11.0 ± 9.1 | 0.350 | 53 | 56 | 22 |
| CD3+CD56−CD16− | 87.0 ± 8.1 | 87.2 ± 7.1 | | 79.5 ± 12.9 | 0.016 | 53 | 56 | 22 |
| CD3+CD56−CD44+ | 7.0 ± 6.1 | 6.1 ± 4.8 | | 13.2 ± 10.5 | 0.025 | 28 | 38 | 12 |
| CD3+CD56−CD44− | 87.1 ± 6.1 | 88.5 ± 6.2 | | 78.0 ± 13.9 | 0.049 | 28 | 38 | 12 |
| CD3−CD56−HLADR− | 29.7 ± 15.6 | 42.7 ± 19.6 | 0.050 | 29.3 ± 21.3 | | 15 | 17 | 6 |
| CD3+CD56−CD122+ | 12.1 ± 7.5 | 11.9 ± 6.3 | | 21.7 ± 14.0 | 0.005 | 27 | 33 | 16 |
| CD3+CD56−CD122− | 81.9 ± 8.2 | 83.0 ± 6.8 | | 68.0 ± 21.7 | 0.024 | 27 | 33 | 16 |
| CD4−CD16− | 51.5 ± 12.9 | 59.1 ± 12.7 | 0.033 | 49.3 ± 21.4 | | 24 | 31 | 11 |
| CD14+CD13+CD16b− | 62.7 ± 20.7 | 56.2 ± 25.8 | | 38.2 ± 26.4 | 0.011 | 19 | 26 | 10 |
| CD16+ | 27.4 ± 12.4 | 30.0 ± 16.2 | | 35.4 ± 19.5 | | 58 | 62 | 23 |
| CD45RA+ | 28.3 ± 9.1 | 27.6 ± 9.0 | | 27.9 ± 16.0 | | 56 | 60 | 25 |
| CD45RO+ | 38.4 ± 13.6 | 38.0 ± 15.5 | | 44.6 ± 18.1 | | 50 | 54 | 24 |
| CD13+ | 24.8 ± 12.7 | 25.5 ± 14.7 | | 31.3 ± 20.3 | | 47 | 57 | 22 |

| Leukocyte Subsets | area under ROC curve | P | Cutoff point | Specificity | Sensitivity | Odds ratio | (CI)[4] |
|---|---|---|---|---|---|---|---|
| CD3−CD44− | 0.766 | 0.007 | >48 | 52 | 92 | 12.9 | (1.4–113.8) |
| CD3+HLADR+ | 0.587 | | <5.5 | 67 | 48.3 | | |
| CD3+CD45RO+ | 0.565 | | <15 | 37.3 | 71 | | |
| CD4+CD13+ | 0.658 | | <1.7 | 50 | 79 | 3.8 | (1.0–13.8) |
| CD13+HLADR+ | 0.740 | 0.021 | <5 | 54 | 92 | 13 | (1.4–117.2) |
| CD14−HLADR+ | 0.679 | | <13 | 57 | 75 | | |
| CD56+HLADR+ | 0.741 | 0.018 | <1.7 | 75 | 71 | 7.2 | (1.5–33.6) |
| CD56−CD44− | 0.708 | 0.041 | <65 | 58 | 83 | 6.8 | (1.2–37.5) |
| CD3−CD4+CD45RA− | 0.668 | 0.021 | <0.7 | 84 | 40 | 3.4 | (1.1–10.7) |
| CD3+CD8−HLADR+ | 0.701 | 0.009 | >14.8 | 55 | 73 | 3.3 | (1.1–10.1) |
| CD3+CD8+HLADR− | 0.691 | 0.013 | <5 | 78 | 59 | 5.0 | (1.6–15.4) |
| CD3+CD56+CD16+ | 0.670 | 0.024 | >1.8 | 49 | 77 | 3.5 | (1.0–10.3) |
| CD3+CD56−CD16+ | 0.698 | 0.009 | >9 | 84 | 50 | 5.4 | (1.7–17.3) |
| CD3+CD56−CD16− | 0.695 | 0.010 | <83 | 81 | 50 | 4.1 | (1.4–12.5) |
| CD3+CD56−CD44+ | 0.721 | 0.034 | >5 | 42 | 92 | | |
| CD3+CD56−CD44− | 0.668 | | <81 | 83 | 58 | 7.0 | (1.5–33.7) |
| CD3−CD56−HLADR− | 0.706 | 0.047 | >36 | 73 | 59 | | |
| CD3+CD56−CD122+ | 0.715 | 0.024 | >20 | 87 | 50 | 6.7 | (1.4–31.7) |
| CD3+CD56−CD122− | 0.715 | 0.024 | <76.5 | 71 | 63 | 4.0 | (1.1–15.5) |
| CD4−CD16− | 0.659 | 0.045 | >58 | 76 | 47 | | |
| CD14+CD13+CD16b− | 0.753 | 0.035 | <61 | 69 | 80 | 8.8 | (1.3–57.4) |
| CD16+ | 0.603 | | >39 | 85 | 39 | 3.5 | (1.2–10.5) |
| | | | >27 | 50 | 51 | | |
| CD45RA+ | 0.562 | | <23.5 | 75 | 48 | 2.8 | (1.0–7.5) |
| CD45RO+ | 0.620 | | >52 | 88 | 43 | 4.4 | (1.3–14.4) |
| CD13+ | | | >29 | 68 | 34 | | |

[1]P value obtained in a student "t" test when mean % of leukocyte subsets found in patients with endometriosis stage I–II was compared to normal controls.
[2]P value obtained in a student "t" test when mean % of leukocyte subsets found in patients with endometriosis stage III–IV was compared to normal controls.

TABLE 6

Peripheral blood leukocyte populations used as markers to discriminate between patients with endometriosis stage I–II or stage III–IV and normal subjects

| Leukocyte Subsets | Mean proportion (% ± s.d.) of leukocyte subsets | | | | | Number of samples tested | | |
|---|---|---|---|---|---|---|---|---|
| | Controls | Endo stage I–II | P[1] | Endo stage III–IV | P[2] | Control | Endo I–II | Endo III–IV |
| CD3−CD57+CD44− | 12.5 ± 6.2 | 14.9 ± 7.5 | 0.030 | 12.2 ± 6.9 | | 84 | 81 | 33 |
| CD14−CD13−HLADR− | 85.6 ± 5.0 | 87.6 ± 3.9 | 0.016 | 85.9 ± 3.3 | | 77 | 54 | 28 |
| CD14−CD20+CD44− | 5.7 ± 2.9 | 4.7 ± 2.6 | 0.043 | 5.6 ± 2.7 | | 65 | 50 | 23 |
| HLADR+ | 21.6 ± 6.0 | 21.7 ± 6.6 | | 23.8 ± 6.7 | 0.037 | 120 | 102 | 52 |
| CD3+CD8− | 49.9 ± 8.5 | 49.0 ± 9.2 | | 46.3 ± 8.8 | 0.012 | 122 | 113 | 53 |
| CD3+CD44− | 60.2 ± 8.6 | 59.2 ± 8.8 | | 57.2 ± 8.0 | 0.047 | 111 | 98 | 45 |
| CD3+HLADR− | 63.3 ± 8.7 | 63.0 ± 9.1 | | 59.6 ± 7.9 | 0.009 | 121 | 102 | 52 |
| CD3−HLADR+ | 18.1 ± 5.8 | 18.7 ± 6.5 | | 20.8 ± 6.9 | 0.010 | 121 | 102 | 52 |
| CD3+CD16+ | 9.3 ± 13.3 | 8.4 ± 12.1 | | 6.0 ± 4.3 | 0.016 | 123 | 113 | 53 |
| CD3−CD57− | 28.3 ± 6.9 | 29.0 ± 7.2 | | 32.3 ± 9.5 | 0.004 | 113 | 101 | 45 |
| CD4−HLADR+ | 19.8 ± 6.0 | 19.8 ± 6.2 | | 22.0 ± 6.6 | 0.036 | 112 | 96 | 49 |
| CD4+CD45RA− | 31.4 ± 8.1 | 29.7 ± 7.2 | | 27.7 ± 8.5 | 0.006 | 125 | 114 | 54 |
| CD4+CD45RO+ | 19.5 ± 5.6 | 20.5 ± 6.4 | | 16.2 ± 4.3 | 0.029 | 27 | 31 | 19 |
| CD13−CD16+ | 18.9 ± 8.2 | 16.8 ± 8.7 | | 14.3 ± 3.1 | 0.035 | 21 | 28 | 9 |
| CD14−CD69− | 81.0 ± 6.1 | 77.4 ± 9.1 | | 76.0 ± 6.7 | 0.031 | 20 | 32 | 14 |
| CD20−HLADR− | 79.3 ± 5.2 | 78.5 ± 7.0 | | 77.1 ± 6.6 | 0.025 | 106 | 97 | 44 |
| CD57−CD44+ | 17.2 ± 5.5 | 18.3 ± 6.4 | | 19.7 ± 7.7 | 0.046 | 84 | 82 | 35 |
| CD3−CD4+CD45RA− | 6.9 ± 4.4 | 6.4 ± 4.0 | | 5.4 ± 3.5 | 0.043 | 122 | 109 | 50 |
| CD3−CD8−CD44+ | 37.2 ± 11.9 | 37.2 ± 12.7 | | 43.2 ± 12.6 | 0.019 | 87 | 80 | 32 |
| CD3−CD57−CD44+ | 38.5 ± 12.1 | 40.3 ± 12.5 | | 44.0 ± 12.7 | 0.029 | 84 | 81 | 33 |
| CD14+CD20+CD44+ | 2.1 ± 1.3 | 2.1 ± 1.5 | | 1.4 ± 0.7 | 0.001 | 65 | 52 | 23 |

| Leukocyte Subsets | area under ROC curve | P | Cutoff point | Specificity | Sensitivity | Odds ratio | (CI)[4] |
|---|---|---|---|---|---|---|---|
| CD3−CD57+CD44− | 0.586 | | >15.6 | 74 | 43 | 2.1 | (1.1–4.1) |
| CD14−CD13−HLADR− | 0.637 | 0.008 | >88.3 | 74 | 47 | 2.6 | (1.1–5.3) |
| CD14−CD20+CD44− | 0.607 | 0.049 | <4.5 | 66 | 53 | 2.2 | (1.0–4.7) |
| HLADR+ | 0.586 | | >24.5 | 73 | 45 | 2.2 | (1.1–4.5) |
| CD3+CD8− | 0.654 | 0.002 | <51.5 | 48 | 85 | 5.2 | (2.2–12.1) |
| CD3+CD44− | 0.605 | 0.047 | <61.2 | 51 | 73 | 2.8 | (1.3–6.1) |
| CD3+HLADR− | 0.628 | 0.010 | <63.5 | 55 | 73 | 3.2 | (1.5–6.6) |
| CD3−HLADR+ | 0.607 | 0.030 | >21.5 | 73 | 45 | 2.3 | (1.1–4.6) |
| CD3+CD16+ | 0.528 | | >3.7 | 31 | 81 | | |
| CD3−CD57− | 0.644 | 0.007 | >28 | 53 | 71 | 2.7 | (1.2–5.7) |
| CD4−HLADR+ | 0.588 | | >19.3 | 48 | 67 | | |
| CD4+CD45RA− | 0.625 | 0.010 | <29.5 | 60 | 60 | 2.3 | (1.2–4.5) |
| CD4+CD45RO+ | 0.645 | | <19.8 | 50 | 90 | 8.5 | (1.6–44.5) |
| CD13−CD16+ | 0.698 | | <13 | 86 | 56 | 7.5 | (1.2–45.1) |
| CD14−CD69− | 0.729 | 0.025 | <82 | 50 | 86 | 6.0 | (1.1–34.0) |
| CD20−HLADR− | 0.573 | | <80.3 | 41 | 72 | | |
| CD57−CD44+ | 0.573 | | >21.6 | 80 | 40 | 2.7 | (1.1–6.7) |
| CD3−CD4+CD45RA− | 0.587 | | <5.5 | 59 | 61 | 2.3 | (1.1–4.5) |
| CD3−CD8−CD44+ | 0.588 | | >40.5 | 54 | 63 | | |
| CD3−CD57−CD44+ | 0.575 | | >44 | 63 | 58 | | |
| CD14+CD20+CD44+ | 0.647 | | <2.1 | 39 | 91 | 6.4 | (1.3–30.9) |

[1]P value obtained in a student "t" test when mean proportion found in patients with endometriosis stage I–II was compared to normal controls.
[2]P value obtained in a student t test when the % leukocyte subsets found in patients with endometriosis stage III–IV was compared to normal controls.

Cutoff points established for each individual marker are presented in Table 3, 4, 5, 6 and threshold value established for a particular marker combination are presented in Table 1. Any other cutoff points or threshold values providing a valuable diagnostic test for endometriosis are meant to be included in the present invention In accordance with a preferred embodiment of the present invention, there is provided a series of 34 different combinations of endometrial leukocyte markers (Tables 1 and 2), 7 combinations of blood leukocyte markers (Tables 1 and 2) and 4 combinations of endometrial and blood leukocyte markers providing a diagnostic test with levels of sensibility and specificity up to 89 and 90%, respectively. The different marker combinations of the present invention may serve several important clinical needs. Hence in the general population, these markers could be used to evaluate the risk factor to develop endometriosis or to identify women with high likelihood of suffering from the disease. Furthermore in patients with endometriosis, these markers could serve to monitor the disease or to give a prognosis.

Study Subjects and Samples

Uterine endometrial tissues were obtained from 146 subjects undergoing laparoscopy or laparotomy. The experimental group was formed of up to 88 subjects with endometriosis stage I–IV confirmed by laparoscopy or laparotomy and the control group consists of up to 58 healthy subjects who underwent surgery for tubal ligation (or reanastomosis) and had no clinical evidence, nor family history of endometriosis. Table 7 gives details concerning the age, menstrual cycle and indication of laparoscopy or laparotomy for the subjects included in experimental and control groups.

Stromal Cell Preparation From Endometrial Samples

Endometrial tissue samples were mechanically disrupted with a Pyrex™ glass Broeck tissue grinder (Fisher) to obtain a single cell suspension. Stromal cell fraction was isolated by filtration through a 250 μm stainless steel sieve (Millipore) to retain the glandular fraction and was washed

TABLE 7

Description of the experimental groups used in the analysis of endometrial leukocyte populations

| Experimental groups | Number of subjects | Mean age ± s.d. | Menstrual cycle | | Percentage of patients* Indication of laparoscopy | | | |
|---|---|---|---|---|---|---|---|---|
| | | | ES[1]* | LS[2]* | ligation or reanastomosis | Hysterectomy and/or ovariectomy | Diagnostic laparoscopy | Other** |
| Controls | 58 | 34.2 ± 5.3 | 54.5% | 45.5% | 100% | | | |
| Endometriosis | | | | | | | | |
| Stage I–IV | 88 | 34.4 ± 6.8 | 47.0% | 53.0% | 21.6% | 22.7% | 52.3% | 3.4% |
| Stage I–II | 63 | 34.4 ± 7.3 | 50.9% | 49.1% | 28.6% | 22.2% | 47.7% | 1.5% |
| Stage III–IV | 25 | 34.4 ± 5.4 | 36.4% | 63.6% | 4.0% | 24.0% | 64.0% | 8.0% |

[1]Early secretory (days 14–21)
[2]Late secretory (days 22–28)
*% patients among control or endometriosis groups Endometrial biopsies were taken with a Pipet Curette (Milex) (approximately 0.5 g of tissue). All samples were harvested in the secretory phase (day 14–28) of the menstrual cycle as confirmed by histological evaluation. The samples were collected into sterile RPMI-1640 medium (Gibco) supplemented with 2% heat-inactivated fetal calf serum (Bio-Media) and 1% penicillin-streptomycin and kept at 4° C. until cell isolation.

Blood samples were obtained from up to 172 subjects with endometriosis (stage I–IV) confirmed by laparascopy or laparotomy and from up to 132 healthy subjects with no evidence of endometriosis at surgery, and no family history of endometriosis. Blood samples (30 ml) were collected in heparin-tubes (Vacutainer™, Becton Dickinson) and kept at 20° C. until mononuclear cell separation. The age, menstrual dating and indication for laparoscopy of the subjects included in the study are given in Table 8.

twice with 10 ml phosphate buffered saline (PBS) (Sigma) containing 1% BSA (Boehringer Mannheim), 0.1% sodium azide (Fisher) (thereafter called PBS washing buffer).

Isolation of Mononuclear Cells From Peripheral Blood

Blood samples were diluted 1:1 with Hank's Balanced Salt Solution (HBSS) (Gibco), layered on an equal volume of Ficoll-Paque™ (Pharmacia Biotech) and centrifuged at 1500 rpm for 40 minutes at room temperature. Leukocytes were isolated at the interface of Ficoll and HBSS and they were washed in 50 ml of HBSS. Contaminating red blood cells were lysed with 6 ml of ammonium chloride solution (0.15M) (6 minutes at room temperature). The peripheral blood mononuclear cells were then washed twice in 10 ml PBS and resuspended in PBS washing buffer.

Endometrial and Peripheral Blood Leukocyte Surface Antigen Staining

Endometrial stromal cells or peripheral blood mononuclear cells were distributed in 5 ml tubes (1 to 1.5×10[6]

TABLE 8

Description of the subjects included in the study of peripheral blood mononuclear leukocytes

| Experimental groups | Number of subjects | Mean age ± s.d. | Menstrual cycle | | Percentage of patients* Indication of laparoscopy | | | |
|---|---|---|---|---|---|---|---|---|
| | | | Proliferative* | Secretory* | ligation or reanastomosis | Hysterectomy and/or ovariectomy | Diagnostic laparoscopy | Other |
| Control | 132 | 34.30 ± 5.5 | 43.8% | 56.2% | 100% | | | |
| Endometriosis | | | | | | | | |
| Stage I–IV | 172 | 36.40* | 42.8% | 57.2% | 22.1% | 33.7% | 38.9% | 5.3% |
| Stage I–II | 116 | 35.96 ± 6.39 | 41.0% | 59.0% | 31.1% | 30.2% | 37.1% | 1.6% |
| Stage III–IV | 56 | 34.30 ± 5.5 | 46.2% | 53.8% | 3.6% | 41.1% | 42.9% | 12.4% |

*% of patients amongst control or endometriosis groups cells/tube) or in 96 well plates ($5 \times 10^5$ cells/well), respectively and incubated in the presence of 0.1 µg of human γ-globulin for 5 minutes at room temperature. The cells were then incubated 30 minutes in the dark (at room temperature for endometrial cells and at 4° C. for peripheral blood mononuclear cells) with a panel of 4 different mouse monoclonal antibodies (MAbs) in a total volume of 100 µl. The cell samples were stained with mouse anti-human CD45 MAbs conjugated to peridinin chlorophyl protein (PerCP) and with several sets of three different mouse MAbs labeled with distinct fluorochromes (fluorescein isothiocyanate —FITC—, phycoerythrin —PE or with phycoerythrin-texas red —ECD—) directed toward cell surface markers for specific cell populations such as T lymphocytes, B lymphocytes, NK cells, macrophages and/or activation markers (Table 9).

TABLE 9

Description of mouse monoclonal antibodies used for immunophenotyping

| Specificity | Clone | Isotype | Supplier | Fluorochrome |
|---|---|---|---|---|
| CD3 | HIT3A | mouse IgG2a | Beckman/Coulter | ECD |
| CD4 | SK3 | mouse IgG1 | Becton Dickinson | PE |
| CD5 | BL1A | mouse IgG2a | Beckman/Coulter | FITC |
| CD8 | SK1 | mouse IgG1 | Becton Dickinson | PE |
| CD13 | SJ1D1 | mouse IgG1 | Beckman/Coulter | RPE |
| CD14 | RM052 | mouse IgG2a | Beckman/Coulter | PE |
| CD16 | NKP15 | mouse IgG1 | Becton Dickinson | FITC |
| CD16B | 1D3 | mouse IgM | Beckman/Coulter | FITC |
| CD20 | H299 | mouse IgG2a | Beckman/Coulter | RDI |
| CD36 | SMf | mouse IgM | Sigma | RPE |
| CD44 | L178 | mouse IgG1 | Becton Dickinson | FITC |
| CD45 | 2D1 | mouse IgG1 | Becton Dickinson | PerCP |
| CD45-RA | ALB11 | mouse IgG1 | Beckman/Coulter | FITC |
| CD45-RO | UCH1 | mouse IgG2a | Beckman/Coulter | FITC |
| CD56 | N901(NKH-1) | mouse IgG1 | Beckman/Coulter | PE |
| CD57 | VC1.1 | mouse IgM | Sigma | RPE |
| CD69 | L78 | mouse IgG1 | Becton Dickinson | FITC |
| CD122 | 2RB | mouse IgG1 | Beckman/Coulter | FITC |
| HLA-DR | L243 | mouse IgG2a | Becton Dickinson | FITC |

Table 10 below lists the distribution of the antigens listed in Table 9.

TABLE 10

Main distribution of antigens

| Antigen | Main Cell Distribution |
|---|---|
| CD3 | Expressed on all mature T cells associated with TCR complex (α/b, γ/δ) |
| CD4 | Expressed on T helper lymphocytes. It can be also expressed on cells of the monocyte/macrophage lineage |
| CD5 | Found on all mature T lymphocytes and a subset of B lymphocytes |
| CD8 | Found on a subset of T lymphocytes called suppressor/cytotoxic T cells. |
| CD13 | Detected on most cells of myeloid origin polymorphonuclear cells or cells of the monocyte/macrophage lineage. Member of metalloproteinase family |
| CD14 | Expressed strongly on the surface of monocytes Found on most tissue macrophages Weakly expressed on the surface of granulocytes and B lymphocytes Receptor for lipopolysacharride (LPS) and LPS binding protein |
| CD16 | Expressed mainly on NK cells, monocytes macrophages and polymorphonuclear leukocytes Low affinity receptor for IgG |

TABLE 10-continued

Main distribution of antigens

| Antigen | Main Cell Distribution |
|---|---|
| CD16b | Found on granulocytes including polymorphonuclear cells (PMN) |
| CD20 | Present on all B lymphocytes |
| CD36 | Expressed on platelets, monocytes or macrophages, microvascular endothelial cells, mammary endothelial cells, during stages of erythroid cell development |
| CD44 | Widely expressed on the surface of most cell types. Including most leukocytes and epithelial cells. Family of core/link peptidoglycan |
| CD45 | Present on the surface of all leukocytes |
| CD45RA | Isoforms of CD45 Found on naive/resting T cells Also expressed on B lymphocytes and monocytes |
| CD45RO | Isoforms of CD45 expressed on memory/activated T cells also expressed on monocytes |
| CD56 | Marker for NK cells Can also be found on a population of T lymphocytes |
| CD57 | Found on a subset of cells with natural killer activity |
| CD69 | Expressed on activated leukocytes including T cells, B cells, NK cells, neutrophils, eosinophils and cells of the monocyte/macrophage lineage. Activation marker detected early after cell activation |
| CD122 | Expressed on NK cells B, T lymphocytes or monocytes/macrophages Component of the IL-15 receptor |
| HLADR+ | HLA class II molecule Found on antigen presenting cells or on other cells upon activation such as T cells. |

Blood cells were washed twice with 0.15 ml of PBS washing buffer. Endometrial cell samples were incubated with a red blood cell lysing solution, (FACS™ Lysing Solution, Becton Dickinson) for 10 minutes at room temperature in the dark and washed with 3 ml of PBS washing buffer. Endometrial and blood cells were fixed in 1% paraformaldehyde (diluted in PBS) at a concentration of $1 \times 10^6$ cells/ml and kept at 4° C. in the dark until the immunofluorescence reactivity was determined by flow cytometry.

Flow Cytometry Analysis

The immunofluorescence reactivity was carried out on a Coulter EPICS XL™ flow cytometer (Coulter Corporation, Hialeah, Fla.) equipped with an argon laser operating at 488 nm, 15 mW and detectors at 525, 575, 610, and 675 nm. Calibration of the flow cytometer parameters for forward scatter, side scatter and fluorescence were the same for all the samples. Cells expressing CD45 pan leukocyte antigen were gated using the Coulter system II software. The percentage of cells bearing markers for T, B lymphocytes, macrophages or NK cells and/or activation markers was evaluated within the CD45 positive populations only. A minimum of 6000 CD45+ cells were analyzed for each sample.

Use of Leukocyte Markers in a Diagnostic Test for Endometriosis

Figure 1:
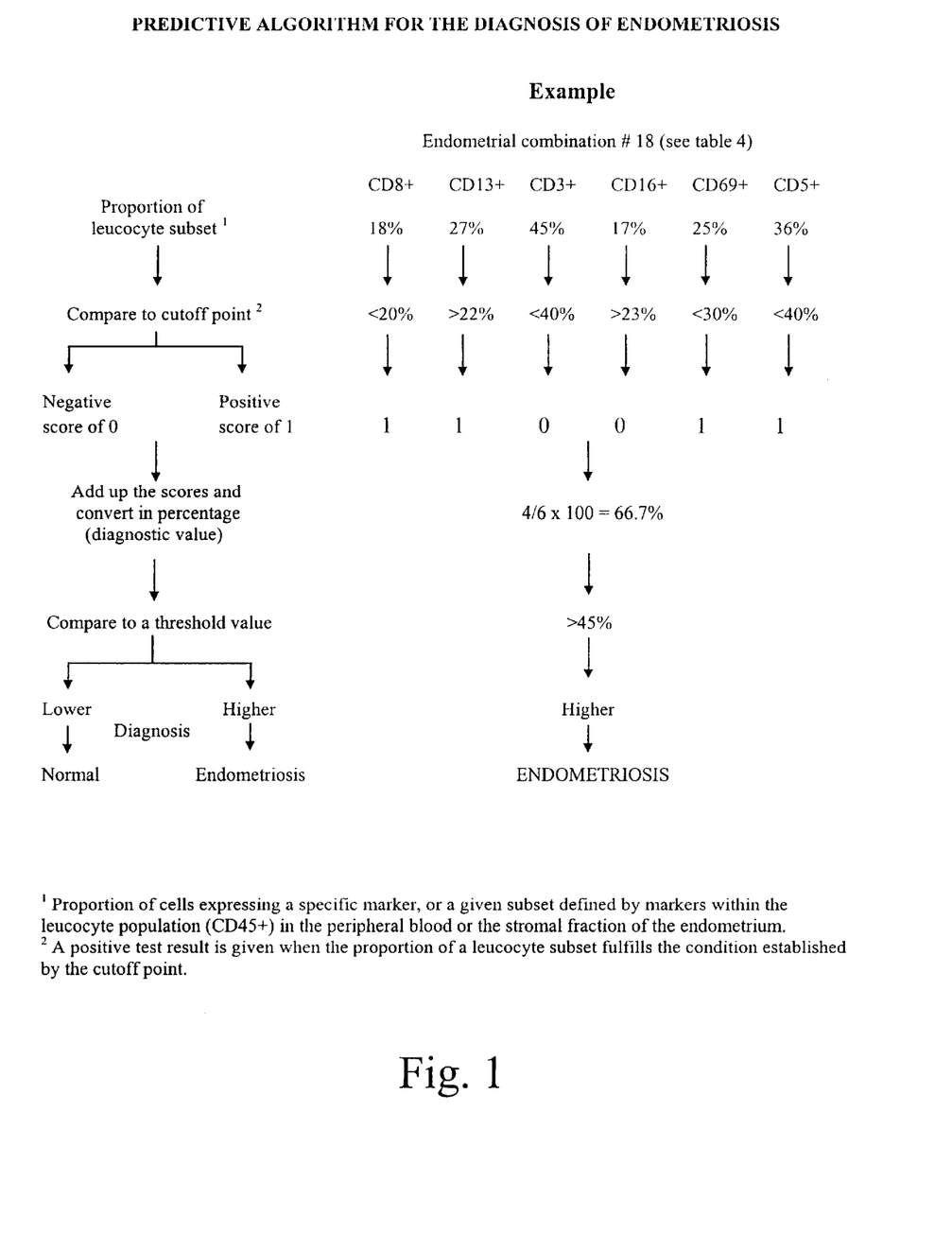
FIG. 1 illustrates a predictive algorithm for the diagnosis of endometriosis.

A cutoff point was established for the proportion of the endometrial or blood leukocyte subpopulations identified as diagnostic markers. The value obtained for each marker is compared to the cutoff point (FIG. 1). A positive result was given when the proportion of a particular leukocyte subset fulfills the condition established by the cutoff point (for example<40% for CD3+ cells). When these markers are used in combination, a positive result for each marker gives a score of 1, whereas a negative result gives a score of 0. A diagnosis of endometriosis is given, when the final diagnostic score obtained from adding the results of all the markers of a particular combination is higher than a predetermined threshold value. The levels of sensibility and/or specificity measured for the marker combination represents the number of positive test results obtained among the patients already confirmed with endometriosis and the number of negative test results among the subjects within the control group, respectively.

Endometrial and blood leukocyte markers can be used in combinations in logistic regression model:

$$P(r) = \frac{e^{c+B1*(marker1)+B2*(marker2)+\ldots Bn*(marker\,n)}}{1+e^{c+B1*(marker1)+B2\pm(marker2)+\ldots Bn\pm(marker\,n)}}$$

Where:
P(r)=probability of having endometriosis
c=constant established for a particular combination
B=coefficient of regression
n total number of markers in the combination The probability of having endometriosis (P(r)) is then compared to a threshold value that provides the best discriminative value. A positive diagnosis of endometriosis is given when the P(r) value exceeds the threshold value established for a particular combination of markers. Alternatively, a negative diagnosis of endometriosis is given when the P(r) value is lower than the threshold value.

Results

Endometrial and blood leukocyte subsets defined as good potential markers for the diagnosis of endometriosis are presented in Tables 3 and 4 respectively. Selection of these markers was done on the basis of 1) a significant difference in the mean proportion of leukocyte subsets between patients with endometriosis (stage I–IV) and control groups; 2) several endometrial and blood leukocyte markers were also selected according to the area under the ROC curve (>0.500), an indication of the discriminative value of the markers. The ROC curve allowed the determination of one or more cutoffs (proportion % of leukocyte subpopulations) that best discriminate between patients with endometriosis (stage I–IV) and normal controls. In an attempt to use these differences for identifying patients with endometriosis, a positive test result was given when the proportion measured for a particular leukocyte subset fulfills the condition established by the cutoff point (for example<40% for CD3+ cells). The levels of specificity and sensibility were calculated for each marker used alone to diagnose endometriosis and are presented in Table 3 (for endometrial leukocyte markers) and Table 4 (for blood leukoyce markers). Moreover, 3) a significant odds ratio calculated with a particular cutoff point gave an additional indication that the leukocyte markers selected in Tables 3 and 4 are associated with an increased risk to develop endometriosis and can, thus, be used for identifying women with high likelihood of suffering from endometriosis.

The mean proportion of some endometrial (Table 5) and blood (Table 6) leukocyte subsets was found to be significantly modulated only in patients with stage I–II endometriosis or with stage III–IV endometriosis when compared to normal controls. These markers remain good candidates for a diagnostic test for endometriosis, but their use may be limited to a specific stage of the disease.

Several of endometrial and blood leukocyte markers were found to be even more reliable as diagnostic markers when they are analyzed in combination with other markers. Table 1 gives a series of 33 combinations in which endometrial or blood leukocyte markers are used in a diagnostic test for endometriosis. For each marker, a positive test result (as described above; see also FIG. 1) gives a score of 1, whereas a negative test result gives a score of 0. The final diagnostic value obtained from adding the scores of all the markers of a particular combination is then compared to a threshold value, which is indicated in Table 1. A diagnosis of endometriosis is given, when the diagnostic value exceeds the threshold value established for each set of combination markers. The use of leukocyte marker subsets in combination in this new method clearly improves the levels of sensibility and/or specificity for diagnosing endometriosis. Table 1 also provides 4 examples showing that blood leukocyte markers, when used in combination with endometrial markers, can also increase the predictive value of the diagnostic test.

The present invention also demonstrate that logistic regression models can also be used to combine endometrial as well as blood leukocyte markers for the development of a predictive model of endometriosis (Table 2). In some cases, these models need to be adjusted with risk factors associated with endometriosis such as the length of the menstrual cycle, the duration of menstruation, pain (during intercourse, menstruation or in other circumstances) and age. In some instances, these factors were shown to increase the predictive value of the model.

The present invention identifies several examples of marker combinations, which give rise to diagnostic methods yielding improved levels of sensibility and specificity. Indeed, the different marker combinations of the present invention may serve different clinical applications including screening, diagnosis, monitoring and prognosis of endometriosis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. For example, other blood or endometrial markers, alone or in combination, might also be suitable to practice the method of the present invention, and are thus intended to be included in the present invention.

What is claimed is:

1. A method for determining likelihood of endometriosis in a female subject, comprising:
   a) obtaining from said female subject a sample of blood;
   b) measuring in said sample a proportion of at least one specific population of blood leukocytes expressing or not expressing at least one specific surface molecule among total blood leukocytes, said specific population of blood leukocytes being selected from the populations of blood leukocytes defined in the following Table B; and

TABLE B

| Population of blood leukocytes | Proportion of the population of leukocytes in the female subject as compared to the cutoff value that is indicative of an increased likelihood of endometriosis |
|---|---|
| CD3 − CD44 + | Higher |
| CD3 − CD69 + | Higher |
| CD3 − CD45RO + | Higher |
| CD3 − CD45RA − | Higher |
| CD4 − CD69 + | Higher |
| CD14 + CD44 + | Higher |
| CD14 + HLADR + | Lower |
| CD20 − CD44 + | Higher |
| CD36 − HLADR + | Lower |
| CD3 − CD57 − CD44 − | Lower | c) comparing the quantitative level measured at step (b) to a predetermined cutoff value for evaluating whether said measured proportion is higher or lower than the cutoff value; wherein a correlation as defined in Table B between the measured proportion and the cutoff value is indicative of an increased likelihood of endometriosis in said female subject as compared to an endometriosis-free female subject.

2. A method for determining likelihood of endometriosis in a female subject, comprising the steps of:

a) obtaining uterine endometrial tissues from said female subject;

b) measuring said tissues for a quantitative level of a population $CD3^-CD45RA^-$ endometrial leukocytes; and c) comparing the quantitative level measured in step (b) to a predetermined cut-off value,
wherein a higher quantitative level of said population of leucocytes as compared to the cut-off value is indicative of an increased likelihood of endometriosis in said female subject as compared to an endometriosis-free female subject.

3. The method of claim 2, further comprising the step of measuring the quantitative level of at least one further population of endometrial leukocytes selected from the group consisting of: CD3−HLADR−, CD3+, CD56−CD16+, CD3+CD16−, CD3+CD56−, and CD16+.

* * * * *

UNITED STATES PATENT AND TRADEMARK OFFICE
CERTIFICATE OF CORRECTION

PATENT NO. : 6,743,595 B1
DATED : June 1, 2004
INVENTOR(S) : Diane Gosselin et al.

It is certified that error appears in the above-identified patent and that said Letters Patent is hereby corrected as shown below:

<u>Column 29,</u>
Line 13, "CD14+HLADR+ Lower" should read -- CD14-HLADR+ Lower --.
Before line 14, add -- CD20+HLADR+ Lower --.

Signed and Sealed this

Seventh Day of February, 2006

JON W. DUDAS
*Director of the United States Patent and Trademark Office*